(12) United States Patent
Wong et al.

(10) Patent No.: US 11,923,047 B2
(45) Date of Patent: *Mar. 5, 2024

(54) METHOD FOR DETERMINING INTERACTION SITES BETWEEN BIOSEQUENCES

(71) Applicants: Andrew Ka-Ching Wong, Waterloo (CA); Ho Yin Sze-To, Waterloo (CA); Peiyuan Zhou, Waterloo (CA)

(72) Inventors: Andrew Ka-Ching Wong, Waterloo (CA); Ho Yin Sze-To, Waterloo (CA); Peiyuan Zhou, Waterloo (CA)

( * ) Notice: Subject to any disclaimer, the term of this patent is extended or adjusted under 35 U.S.C. 154(b) by 216 days.

This patent is subject to a terminal disclaimer.

(21) Appl. No.: 17/345,699

(22) Filed: Jun. 11, 2021

(65) Prior Publication Data
US 2021/0304842 A1    Sep. 30, 2021

Related U.S. Application Data

(63) Continuation of application No. 15/485,767, filed on Apr. 12, 2017, now Pat. No. 11,074,992.

(60) Provisional application No. 62/390,845, filed on Apr. 12, 2016.

(51) Int. Cl.
| | | |
|---|---|---|
| G01N 33/48 | (2006.01) | |
| G01N 33/50 | (2006.01) | |
| G16B 20/00 | (2019.01) | |
| G16B 20/30 | (2019.01) | |

(Continued)

(52) U.S. Cl.
CPC ............ *G16B 20/30* (2019.02); *G16B 20/00* (2019.02); *G16B 40/00* (2019.02); *G16B 40/30* (2019.02)

(58) Field of Classification Search
CPC ............................ G16B 20/00; G16B 40/00
See application file for complete search history.

(56) References Cited

U.S. PATENT DOCUMENTS 11,074,992 B2 *   7/2021   Wong ..................... G16B 20/00

OTHER PUBLICATIONS

Excoffier et al. Computer programs for population genetics data analysis: a survival guide. Nature Reviews Genetics, vol. 7, pp. 745-758. (Year: 2006).*

(Continued)

*Primary Examiner* — Russell S Negin
(74) *Attorney, Agent, or Firm* — Bhole IP Law; Anil Bhole; Marc Lampert

(57) ABSTRACT

A method and system for determining interaction sites between biosequences is described herein. A dataset of contact data for a plurality of biomolecule pairs is obtained to account their frequency of occurrence. Statistical weights are obtained for each frequency of occurrence. A statistical vector space (SRV) is decomposed through principal component decomposition. The r-vectors of the SRV are re-projected back to a new SRV with a new set of SR coordinates. A feature vector is generated and inputted into a predictor for outputting a likelihood of an interaction site. A method and system for determining significant attribute-value associations (AVAs) from relational datasets is also described. A frequency of occurrence of attribute value pairs and statistical weights may be obtained for each frequency of occurrence. Principal component decomposition and re-projection of AVA vectors may also be performed. The disentangle SR of AVAs could be used to identify AVA related to subgroups/classes.

20 Claims, 25 Drawing Sheets

(51) Int. Cl.
*G16B 40/00* (2019.01)
*G16B 40/30* (2019.01)

(56) References Cited

OTHER PUBLICATIONS

Bernardes et al. A review of protein function prediction under machine learning perspective. Recent Patents on Biotechnology, vol. 7, pp. 122-141. (Year: 2013).*

* cited by examiner

Figure 3A

R2R Contact Frequency Matrix (R2RCFM)

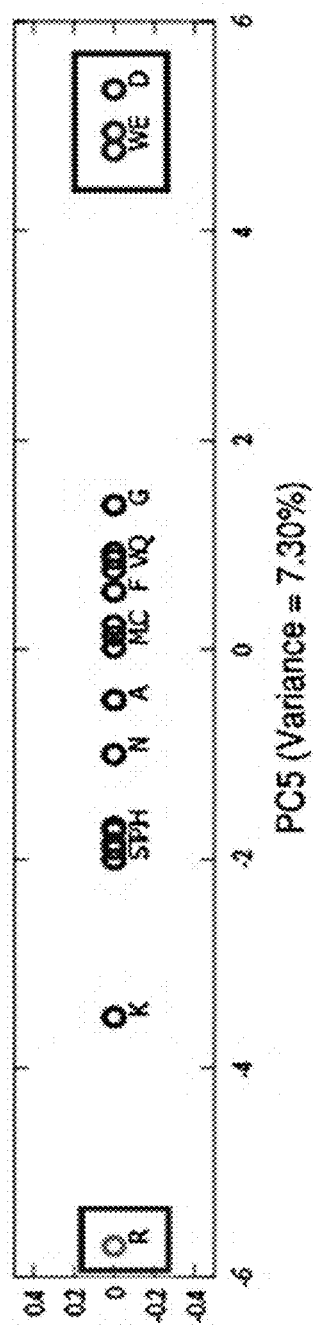

|  | Accuracy | Precision | Recall | Specificity | F1 | AUC |
|---|---|---|---|---|---|---|
| P2K | 0.850 | 0.081 | 0.365 | 0.851 | 0.069 | 0.699 |
| PPiPP | 0.780 | 0.013 | 0.406 | 0.780 | 0.016 | 0.647 |

Figure 7A

|  | Accuracy | Precision | Recall | Specificity | F1 | AUC |
|---|---|---|---|---|---|---|
| P2K | 0.999 | 0.062 | 0.038 | 1.000 | 0.038 | 0.699 |
| PPiPP | 0.995 | 0.004 | 0.005 | 0.995 | 0.002 | 0.647 |

Figure 7B

|  | TP | FP | TN | FN | Accuracy | Precision | Recall | Specificity | F1 | AUC |
|---|---|---|---|---|---|---|---|---|---|---|
| P2K | 4 | 1 | 42795 | 0 | 1.000 | 0.800 | 1.000 | 1.000 | 0.889 | 1.000 |
| PPiPP | 0 | 5 | 42791 | 4 | 1.000 | 0.000 | 0.000 | 1.000 | 0.000 | 0.898 |

Figure 7C

|  | TP | FP | TN | FN | Accuracy | Precision | Recall | Specificity | F1 | AUC |
|---|---|---|---|---|---|---|---|---|---|---|
| P2K | 4 | 1 | 14955 | 4 | 1.000 | 0.800 | 0.500 | 1.000 | 0.615 | 0.952 |
| PPiPP | 0 | 5 | 14951 | 8 | 0.999 | 0.000 | 0.000 | 1.000 | 0.000 | 0.905 |

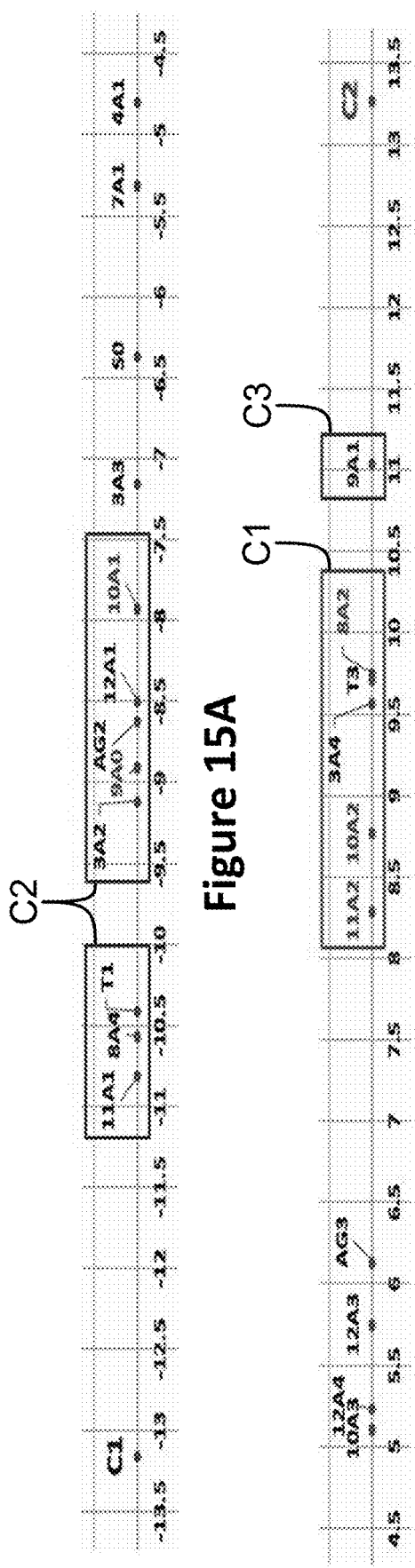
Figure 15A
Figure 15B
Figure 15C

| Hidden AVAs / IR | Freq-1 | Freq-2 | SRV | AVAA |
|---|---|---|---|---|
| 10% | 0.83 | 0.83 | 0.83 | 0.83 |
| 20% | 0.83 | 0.83 | 0.83 | 0.83 |
| 30% | 0.83 | 0.83 | 0.83 | 0.83 |
| 40% | 0.83 | 0.83 | 0.83 | 1.00 |
| 50% | 0.83 | 0.83 | 0.83 | 1.00 |
| 60% | 0.83 | 0.83 | 0.83 | 1.00 |
| 70% | 0.66 | 1.00 | 0.83 | 1.00 |
| 80% | 0.66 | 1.00 | 0.83 | 1.00 |
| 90% | 0.41 | 1.00 | 0.83 | 1.00 |
| 100% | 0.41 | 1.00 | 0.83 | 1.00 |

Figure 16

| IR | Freq-1 | Freq-2 | SRV | AVAA |
|---|---|---|---|---|
| no noise | 0.66 | 1.00 | 0.83 | 1.00 |
| 50% | 0.51 | 0.97 | 0.83 | 1.00 |
| 100% | 0.45 | 0.96 | 0.83 | 0.99 |
| 150% | 0.43 | 0.85 | 0.83 | 0.97 |
| 200% | 0.42 | 0.84 | 0.79 | 0.95 |

Figure 17

Attributes a1. age
a2. sex
a3. chest pain type (4 values)
a4. resting blood pressure
a5. serum cholesterol in mg/dl
a6. fasting blood sugar > 120 mg/dl
a7. resting electrocardiographic results (values 0,1,2)
a8. maximum heart rate achieved
a9. exercise induced angina
a10. oldpeak = ST depression induced by exercise relative to rest
a11. the slope of the peak exercise ST segment
a12. number of major vessels (0-3) colored by flourosopy
a13. thal: 3 = normal; 6 = fixed defect; 7 = reversable defect

Attributes types (mixed-mode)

Real: 1, 4, 5, 8, 10, 12
Ordered: 11,
Binary: 2, 6, 9
Nominal: 7, 3, 13

Class 1 Normal   C2 Heart Disease

| SRV | 8A1 | 8A2 | 8A3 | 8A4 | 9A2 | 10A1 | 10A4 | 11A1 | 11A2 | 11A3 |
|---|---|---|---|---|---|---|---|---|---|---|
| 8A1 | -0.83 |  |  |  |  |  |  | -1.60 | 0.96 | 1.81 |
| 8A2 | 1.18 | -2.72 |  |  |  |  |  | -3.45 | 3.59 | -0.07 |
| 8A3 | -0.55 | 3.88 | 0.70 |  |  |  |  | 0.56 | -0.64 | 0.17 |
| 8A4 | 1.38 | -2.27 | -1.00 | 2.07 |  |  |  | 3.35 | -3.10 | -0.92 |
| 9A1 | -0.71 | 3.47 | 0.50 | -2.95 | -2.95 |  |  | 1.91 | -1.75 | -0.59 |
| 9A2 | -0.26 | 0.84 | -0.72 | 1.80 |  | 1.26 |  | -2.73 | 2.49 | 0.65 |
| 10A1 |  | 0.80 | -0.05 | -3.10 | 2.21 | -1.80 | 0.42 | 2.87 | -2.12 | -2.18 |
| 10A2 |  | -3.45 | 0.56 | -0.09 | 1.82 |  |  | -3.76 | 3.70 | 0.46 |
| 10A3 | -1.60 | 3.59 | -0.64 | -0.65 | 0.42 |  | -0.98 | -2.32 | 0.47 | 5.00 |
| 10A4 | 0.96 | -0.07 | 0.17 | -0.32 | 0.85 | 2.87 | -0.95 | -0.98 | -0.95 | 5.11 |
| 11A1 | 1.81 |  |  |  |  | 2.12 |  |  |  |  |
| 11A2 |  |  |  |  |  | -2.18 |  |  |  |  |
| 11A3 |  |  |  |  |  |  |  |  |  |  |

| RSFV1 | 8A1 | 8A2 | 8A3 | 8A4 | 9A1 | 9A2 | 10A1 | 10A2 | 10A3 | 10A4 | 11A1 | 11A2 | 11A3 | C1 | C2 |
|---|---|---|---|---|---|---|---|---|---|---|---|---|---|---|---|
| 8A1 | 0.30 | 0.88 | -0.14 | -0.81 | -0.64 | 0.32 | -0.61 | 0.72 | 0.66 | 0.18 | -0.91 | 0.71 | 0.59 | -1.17 | 1.31 |
| 8A2 | 0.87 | 2.39 | -0.34 | -2.30 | -1.70 | 2.54 | -1.63 | 2.06 | 1.51 | 0.50 | -2.36 | 1.97 | 1.21 | -2.88 | 3.23 |
| 8A3 | -0.17 | -0.35 | 0.03 | 0.40 | 0.29 | -0.41 | 0.23 | -0.37 | -0.03 | -0.08 | 0.27 | -0.31 | 0.09 | 0.48 | -0.54 |
| 8A4 | -0.94 | -2.39 | 0.30 | 2.40 | 1.82 | -2.53 | 1.61 | -2.18 | -1.17 | -0.52 | 2.22 | -2.01 | -0.75 | 2.74 | -3.07 |
| 9A1 | -0.73 | -1.84 | 0.23 | 1.86 | 1.41 | -2.01 | 1.24 | -1.70 | -0.86 | -0.40 | 1.70 | -1.55 | -0.53 | 2.28 | -2.55 |
| 9A2 | 0.93 | 2.57 | -0.36 | -2.47 | -1.91 | 2.73 | -1.76 | 2.22 | 1.61 | 0.54 | -2.53 | 2.12 | 1.29 | -3.24 | 3.62 |
| 10A1 | -0.66 | -1.66 | 0.20 | 1.69 | 1.28 | -1.82 | 1.12 | -1.54 | -0.76 | -0.36 | 1.53 | -1.41 | -0.45 | 2.01 | -2.25 |
| 10A2 | 0.76 | 2.11 | -0.30 | -2.02 | -1.57 | 2.24 | -1.44 | 1.81 | 1.35 | 0.44 | -2.09 | 1.73 | 1.10 | -2.61 | 2.92 |
| 10A3 | 0.47 | 1.35 | -0.20 | -1.27 | -0.99 | 1.42 | -0.93 | 1.14 | 0.92 | 0.28 | -1.36 | 1.10 | 0.79 | -1.60 | 1.79 |
| 10A4 | 0.14 | 0.48 | -0.08 | -0.42 | -0.34 | 0.49 | -0.34 | 0.37 | 0.44 | 0.09 | -0.53 | 0.38 | 0.43 | -0.80 | 0.90 |
| 11A1 | -0.93 | -2.36 | 0.29 | 2.36 | 1.80 | -2.56 | 1.59 | -2.16 | -1.15 | -0.51 | 2.19 | -1.98 | -0.74 | 2.81 | -3.14 |
| 11A2 | 0.71 | 1.99 | -0.28 | -1.90 | -1.47 | 2.10 | -1.36 | 1.70 | 1.28 | 0.41 | -1.97 | 1.63 | 1.05 | -2.48 | 2.77 |
| 11A3 | 0.34 | 1.01 | -0.15 | -0.93 | -0.73 | 1.05 | -0.69 | 0.83 | 0.73 | 0.20 | -1.03 | 0.81 | 0.64 | -1.06 | 1.19 |

Figure 19C

| RSRV5 | 8A1 | 8A2 | 8A3 | 8A4 | 9A1 | 9A2 | 10A1 | 10A4 | 11A1 | 11A2 | 11A3 |
|---|---|---|---|---|---|---|---|---|---|---|---|
| 8A1 | -0.69 | -0.61 | 0.04 | 1.06 | | 0.52 | 0.16 | -0.56 | -0.89 | 0.4 | 1.33 |
| 8A2 | -0.89 | -1.08 | 0.07 | 1.38 | | 0.65 | 0.23 | -0.73 | -1.1 | 0.5 | 1.64 |
| 8A3 | 0.11 | 0.25 | -0.05 | -0.22 | | 0.02 | -0.1 | 0.1 | -0.06 | 0.02 | 0.11 |
| 8A4 | 1.18 | 1.67 | -0.17 | -1.95 | | -0.66 | -0.5 | 0.99 | 1.06 | -0.51 | -1.53 |
| 9A1 | -0.29 | -0.28 | 0 | 0.41 | | 0.27 | 0.02 | -0.23 | -0.47 | 0.21 | 0.72 |
| 9A2 | 0.5 | 0.77 | -0.09 | -0.85 | | -0.23 | -0.3 | 0.43 | 0.35 | -0.17 | -0.49 |
| 10A1 | 0.31 | 0.51 | -0.07 | -0.54 | | -0.11 | -0.2 | 0.26 | 0.15 | -0.08 | -0.19 |
| 10A2 | 0.09 | 0.22 | -0.04 | -0.19 | | 0.03 | -0.1 | 0.08 | -0.08 | 0.03 | 0.15 |
| 10A3 | -0.76 | -0.91 | 0.05 | 1.18 | | 0.57 | 0.18 | -0.62 | -0.97 | 0.44 | 1.45 |
| 10A4 | -0.66 | -0.78 | 0.04 | 1.02 | | 0.51 | 0.15 | -0.54 | -0.86 | 0.39 | 1.3 |
| 11A1 | -0.74 | -0.88 | 0.05 | 1.15 | | 0.56 | 0.18 | -0.61 | -0.94 | 0.43 | 1.42 |
| 11A2 | 0.47 | 0.72 | -0.09 | -0.8 | | -0.21 | -0.2 | 0.4 | 0.32 | -0.16 | -0.43 |
| 11A3 | 1.01 | 1.45 | -0.15 | -1.68 | | -0.56 | -0.4 | 0.85 | 0.89 | -0.42 | -1.28 |

Figure 19D

METHOD FOR DETERMINING INTERACTION SITES BETWEEN BIOSEQUENCES

TECHNICAL FIELD

The present disclosure relates generally to determining associations in relational data, and, more particularly, to determining interaction sites between biosequences.

BACKGROUND

Relational datasets can be processed to discover useful associations. The majority of current techniques for processing frequency patterns in data rely on the frequency count directly obtained from the data. As problems in data processing become more complex, the traditional frameworks using frequency counts directly may not reveal as much useful associations in the data as may be desired.

Biosequence interaction may reveal cell fate and molecular basis of diseases and as such the identification of interacting sites between biosequences may assist in drug discovery. Traditionally, these interacting sites are identified through three-dimensional (3D) structures obtained by expensive, time-consuming, and labour-intensive wet-lab experiments. For example, protein-protein interaction is a type of biosequence interaction. Identifying interacting sites, such as residue-residue interaction sites in a protein-protein interaction, are useful for therapeutic intervention such as developing a new antibody.

As such, there is a need for improvement.

SUMMARY

In one aspect, a computer-implemented method for training a machine learning classifier to determine interaction sites between biosequences is provided, the method comprising: obtaining a dataset of contact data for a plurality of biomolecule pairs from a database, each one of the biomolecule pairs composed of a biomolecule ri from a first biosequence and a biomolecule rj from a second biosequence, the contact data corresponding to a separation distance between ri and rj; generating, by a processor, a training set comprising one or more k-dimensional feature vectors for each biomolecule pair (ri, rj), the generating the training set comprising: generating a contact frequency matrix comprising a frequency of occurrence of every biomolecule pair (ri, rj) in the contact data; generating a statistical residual frequency matrix indicating a statistical significance of the frequency of occurrence of each biomolecule pair (ri, rj), wherein the statistical residual frequency matrix is considered as a statistical residual vector space such that each row is a vector having coordinates that are statistical residuals of a given biomolecule interaction with other biomolecules corresponding to a column of the statistical residual vector space; decomposing the statistical residual vector space through principal component decomposition to obtain vector projections on principal components; re-projecting the vector projections on the principal components to re-projected statistical residual vector spaces with new vector positions; and deriving the statistical weights from the re-projected residual vector spaces for each biomolecule pair (ri, rj); generating the k-dimensional feature vector for each biomolecule pair (ri, rj) and its nearest neighbors using at least the statistical weights; and training, by the processor, the machine learning classifier to classify a likelihood that an input biosequence pair is interacting at an interaction site, using the training set.

In another aspect, a system for training a machine learning classifier to determine interaction sites between biosequences is provided, the system comprising: at least one processing unit; and a non-transitory computer-readable memory having stored thereon program instructions executable by the at least one processing unit for: obtaining a dataset of contact data for a plurality of biomolecule pairs from a database, each one of the biomolecule pairs composed of a biomolecule ri from a first biosequence and a biomolecule rj from a second biosequence, the contact data corresponding to a separation distance between ri and rj; generating, by a processor, a training set comprising one or more k-dimensional feature vectors for each biomolecule pair (ri, rj), the generating the training set comprising: generating a contact frequency matrix comprising a frequency of occurrence of every biomolecule pair (ri, rj) in the contact data; generating a statistical residual frequency matrix indicating a statistical significance of the frequency of occurrence of each biomolecule pair (ri, rj), wherein the statistical residual frequency matrix is considered as a statistical residual vector space such that each row is a vector having coordinates that are statistical residuals of a given biomolecule interaction with other biomolecules corresponding to a column of the statistical residual vector space; decomposing the statistical residual vector space through principal component decomposition to obtain vector projections on principal components; re-projecting the vector projections on the principal components to re-projected statistical residual vector spaces with new vector positions; and deriving the statistical weights from the re-projected residual vector spaces for each biomolecule pair (ri, rj); generating the k-dimensional feature vector for each biomolecule pair (ri, rj) and its nearest neighbors using at least the statistical weights; and training, by the processor, the machine learning classifier to classify a likelihood that an input biosequence pair is interacting at an interaction site, using the training set.

DESCRIPTION OF THE DRAWINGS

Reference is now made to the accompanying figures in which:

FIG. 3A is an example of a residue-residue contact frequency matrix;

FIG. 3B is an example of a residue-residue adjusted statistical residual matrix;

FIGS. 4A and 5A are examples of statistical residual vectors projected onto principal component axes;

FIGS. 4B and 5B are examples of re-projected statistical residual vector spaces;

FIG. 6A is a table showing six principal component coordinates for 20 amino acids;

FIG. 6B is a table showing re-projected statistical residual vectors of residue pairs P-E, V-F, K-A, A-V, A-L, F-T and V-I;

FIG. 6C is an example of a feature vector;

FIGS. 7A to 7D are tables illustrating results of a benchmark experiment;

FIG. 11 is a table of observed and expected frequencies of an attribute-value association;

Figures 12, 13:
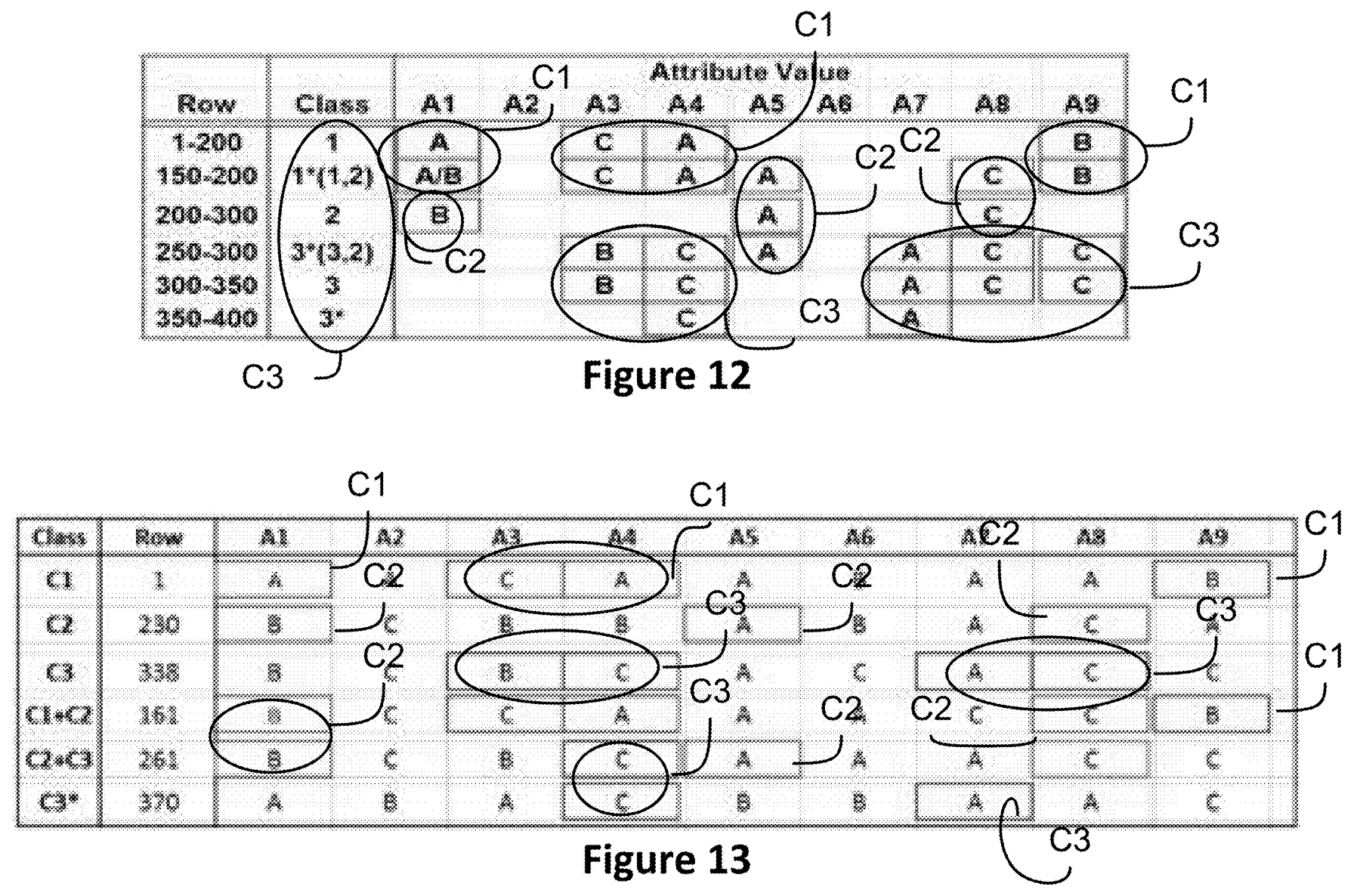

FIG. 12 is a table showing a synthetic dataset with embedded patterns and entangled patterns;

FIG. 13 is a table showing revealed patterns in a sample in an example relational dataset;

FIGS. 14A to 14D are tables showing examples of various attribute-value association groups;

FIGS. 15A to 15C illustrate an example principal component and part of a re-projected statistical residual vector space;

FIGS. 16 and 17 are tables illustrating experimental results;

FIG. 18 is a table showing attributes for an example relational dataset;

FIGS. 19A to 19D are tables showing examples of a disentangled re-projected statistical residual vector space.

It will be noted that throughout the appended drawings, like features are identified by like reference numerals.

DETAILED DESCRIPTION

Figure 1:
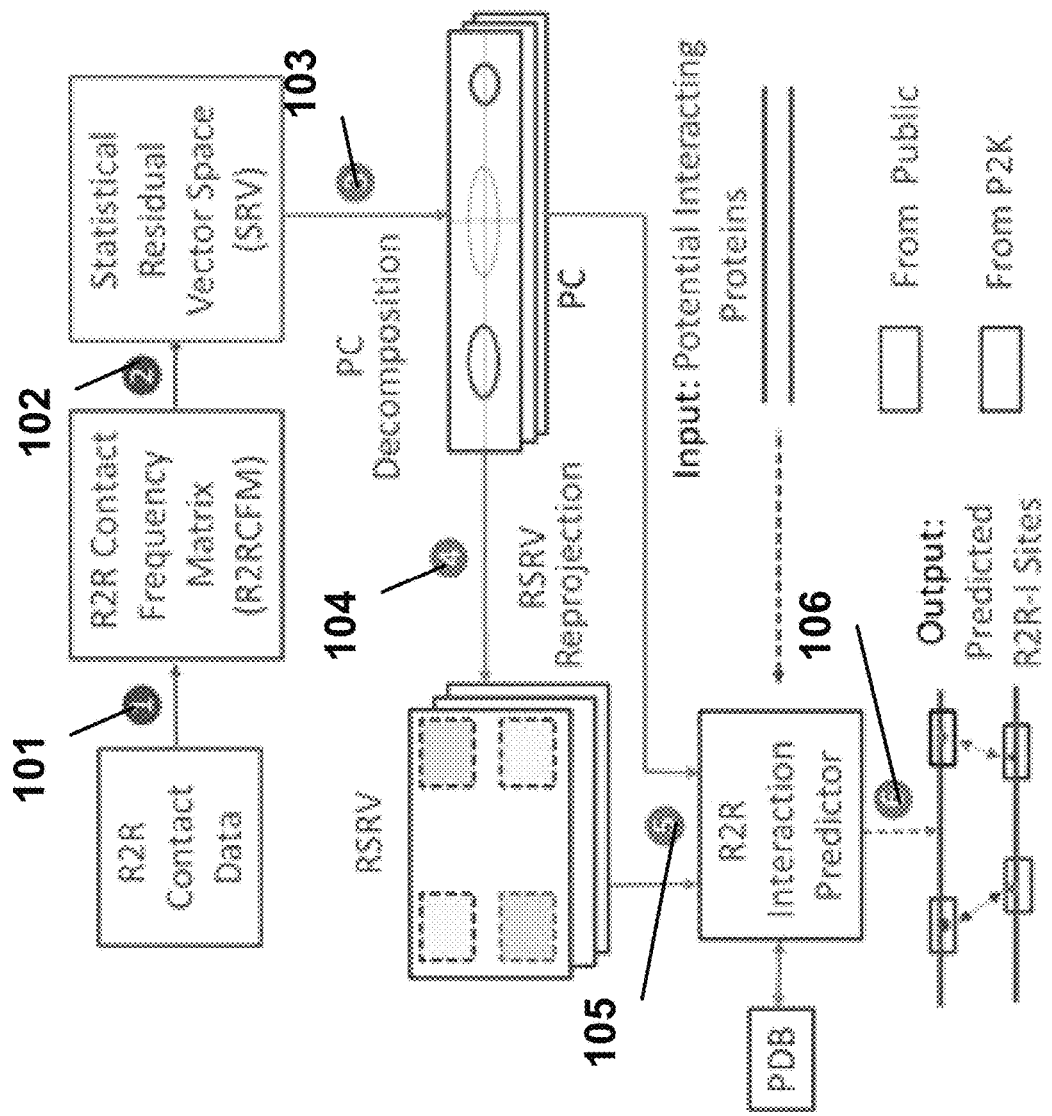
FIG. 1 is a schematic overview for determining interaction sites between biosequences in accordance with an embodiment.
Figure 2:
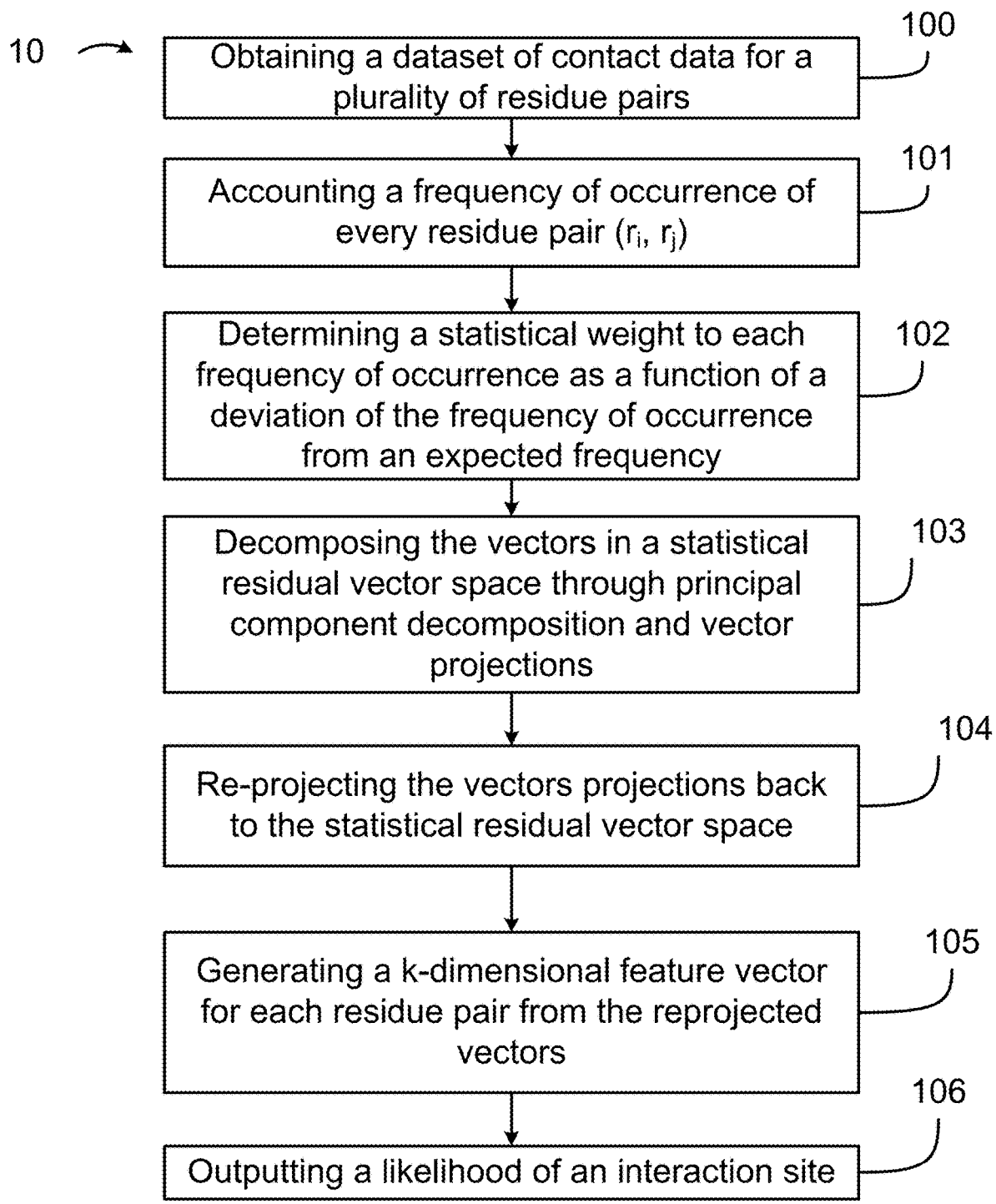
FIG. 2 is a flowchart illustrating an example method for determining interaction sites between biosequences in accordance with an embodiment.

FIG. 1 illustrates a schematic overview of a method for determining interaction sites between biosequences. Each block represents an outcome of a given step of the method, the step itself being represented by the arrows connecting the blocks. The method steps are also illustrated more explicitly in the flowchart 10 of FIG. 2. The method is explained in more detail below with reference to FIGS. 1 and 2.

Step 100: Obtain a Dataset

At step 100, a dataset is obtained. The dataset comprises contact data for a plurality of biomolecule pairs, where each one of the biomolecule pairs composed of a biomolecule $r_i$ from a first biosequence having n biomolecules and a biomolecule $r_j$ from a second biosequence having m biomolecule, where i=1 to n and j=1 to m, in which the contact between $r_i$ and $r_j$ corresponds to a maximum separation distance.

The biosequences may include protein sequences, nucleic acid sequences, DNA sequences, RNA sequences, aptamer sequences, antibody sequences and/or any other suitable biosequences. In this embodiment, the dataset includes data between two protein sequences. The contact data include contact pair information indicating interaction or non-interaction between pairs. In the case that the biosequences are two protein sequences, the contact data may include residue-residue (R2R) contact pairs of the two protein sequences. The R2R contact data may be obtained from a protein-protein (P2P) three-dimensional (3D) interaction complex structure in a protein database.

While the terms "biomolecule" and "residue" are used in various example described in this document, it should be appreciated that these terms may possibly be used interchangeable depending on the type of biosequences in which the method 10 is being applied thereto. For instance, in the case of protein sequences, the term "residue" may be used; while for other biosequences, the term "biomolecule" may be used.

Two biomolecules from different biosequences are considered interacting if the closest distance (also referred to as the separation distance) between the two biomolecules is less than a distance threshold; otherwise, they are considered as non-interacting. In the case of two protein sequences, two residues from different protein chains are considered interacting if the closest distance between them is less than a distance threshold; otherwise, they are considered as non-interacting. In accordance with a specific and non-limiting example of implementation, the distance threshold for the separation distance between two residues may be 6 Å (Angstrom) and the separation distance between two residues may be computed via the Euclidean distance between the C-Beta atoms (e.g., C-Alpha atoms for Gly).

In this document, various examples are provided by use of a specific and non-limiting dataset. This dataset is provided for illustration purposes only and includes 618 non-redundant three-dimensional protein-protein interaction (P2P-I) complexes from the protein databank (PDB), as described in F. Glaser, D. M. Steinberg, I. A. Vakser, and N. Ben-Tal, "*Residue frequencies and pairing preferences at protein-protein interfaces,*" Proteins Struct. Funct. Genet., vol. 43, pp. 89-102, 2001, the contents of which are hereby incorporated by reference. Furthermore, while specific examples are provided herein where the biosequences in the dataset correspond with protein sequences and the contact data correspond with residue-residue (R2R) contact, it should be appreciated that it is for example purposes only and that any suitable biosequences may be used in other practical implementations.

In some embodiments, the dataset may be processed (e.g., pre-processed) to obtain the contact data for the dataset in a suitable format for processing by a system implementing the method 10.

The dataset may be obtained from a database or any other suitable computer readable medium. Obtaining the dataset may refer to receiving the dataset from a local or remote source, or it may refer to acquiring the dataset from a local or remote source.

Step 101: Determine a Frequency of Occurrence

At step 101, a frequency table is obtained by accounting of a frequency of occurrence of every biomolecule pair ($r_i$, $r_j$) in the contact data.

In accordance with an embodiment, determining the frequency of occurrence includes generating a residue-residue contact frequency matrix (R2RCFM) from the dataset. An alphabet set $\Sigma_R$={I, V, L, F, C, M, A, G, T, S, W, Y, P, H, E, Q, D, N, K, R} can be defined to represent $|\Sigma_R|$=20 residues. It should be appreciated that the alphabet set in this example corresponds to 20 residues. A pair of residues, defined as residue pair ($r_i$, $r_j$), can be observed to be at a contact distance closer than a distance threshold in the 3D structures, where $r_i$, $r_j \in \Sigma_R$. Accordingly, each residue pair ($r_i$, $r_j$) has a contact distance that is indicative of a closeness event between the pair of residues. In a specific and non-limiting example considered in this document, the distance threshold for the closeness event is 6 Å. The R2RCFM has $|\Sigma_R| \times |\Sigma_R|$ entries stored therein, where each entry (R2RCFM)$_{i,j}$ records the frequency of the closeness event of the residue pair ($r_i$, $r_j$). The terms "entries" and "entry" may be used synonymously with "indices" and "index" in the various matrices described in this document. The closeness event of a residue pair $(r_i, r_j)$ is indicative of whether or not the contact distance of that residue pair $(r_i, r_j)$ is smaller than the distance threshold. It should be noted that the closeness events are considered to be undirected. Hence, $(r_i, r_j)$ and $(r_j, r_i)$ refer to the same R2R contact and thus $(R2RCFM)_{i,j} = (R2RCFM)_{j,i}$. While 6 Å is used as the distance threshold to determine the closeness between the residues in the example described in this document, it should be appreciated that this threshold is for example purposes only and that other suitable values may be used in other practical implementations.

Figure 3A:
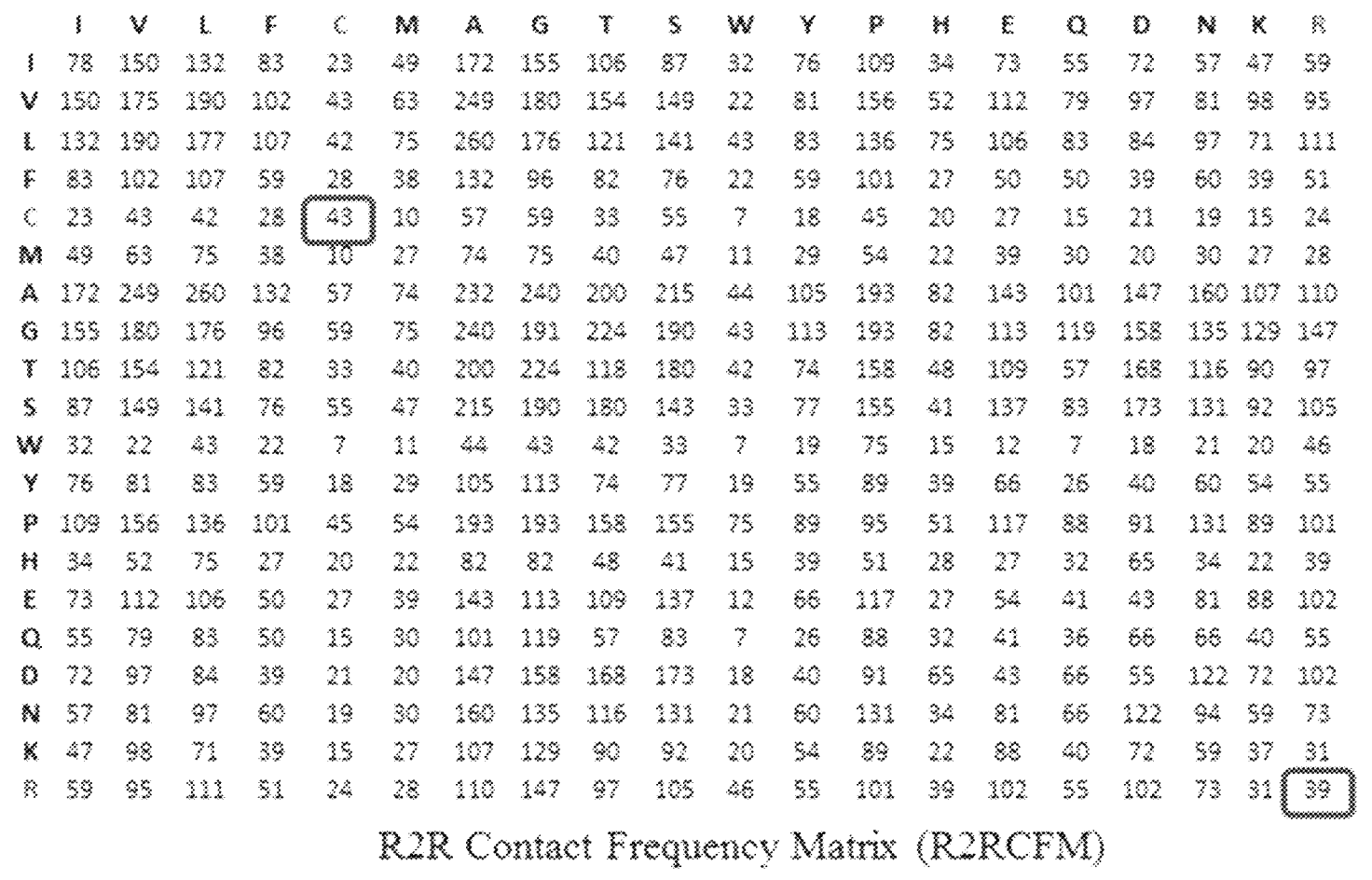

With additional reference to FIG. 3A, an example of the R2RCFM is shown. In this example, the rows and the columns of the R2RCFM correspond to the 20 amino acids in the alphabet set. The numerical value for each entry $(R2RCFM)_{i,j}$ in the R2RCFM indicates the frequency in the form of a numerical count of the closeness event of the residue pair $(r_i, r_j)$ between the 20 amino acids in the R2R contact data of two protein sequences.

Step 102: Conversion of R2R Contact Frequencies into Statistical Residuals

Step 102, includes determining a statistical weight for each frequency of occurrence as a function of a deviation of the frequency of occurrence from an expected frequency to obtain a statistical residual frequency matrix, wherein the statistical residual frequency matrix is considered as a statistical residual vector space such that each row is a vector having coordinates that are statistical residuals of a given biomolecule interacting with other biomolecules.

For example, a statistical weight may be obtained for each frequency of occurrence as a function of a deviation of the frequency of occurrence from an expected frequency if the occurrence is a random happening to obtain a statistical residual frequency table, wherein the statistical residual frequency table is considered as a statistical residual vector space such that each row is a residual vector (r-vector) representing a given residue interacting with other residues with the statistical residual as its coordinates.

Determining a statistical weight may include converting each of the residue-residue contact (R2R-C) frequency in the R2RCFM into a statistical residual (SR). In general terms, the conversion from a frequency count to a SR is to account for how far the observed frequency deviates from its default random mode. To elaborate, if the contact event (which may also be referred to as separation distance) of the residue pair $(r_i, r_j)$ is driven by actual interactions, it should likely be non-random, and thus statistically significant. As such, at this step, a statistical residual $s_{ri,rj}$ (which may also be referred to as a statistical weight) is introduced to measure how the frequency of occurrence of the contact event of the residue pair $(r_i, r_j)$ deviates, positively or negatively, from its expected value if its occurrence were random (e.g., irrelevant to residue-residue interaction (R2R-I)). Thus, the R2R contact event of the residue pair $(r_i, r_j)$ is statistically significant with the statistical residual $s_{ri,rj}$ being greater than $\theta$ or less than $-\theta$, where $\theta$ is a statistical significance threshold. In a specific example of implementation, the statistical significance threshold $\theta$ is set as 1.96, which corresponds to a confidence interval of 95% in Chi-square test. The statistical significance threshold $\theta$ may be set to other values in other practical implementations.

An adjusted standard residual to measure the statistical residual $s_{ri,rj}$ may be adopted. The adjusted standard residual of a R2R contact event can be determined as follows.

Referring to $r_i$ as the $i^{th}$ element in $\Sigma_R$, a frequency of a R2R interaction event involving $r_i$ can be defined as follows:

$$f(r_i) = \sum_{j=1}^{|\Sigma_R|} (R2RCFM)_{i,j}$$

By this, a probability of observing an R2R interaction event involving $r_i$ can be defined as follows:

$$p(r_i) = \frac{f(r_i)}{\sum_{j=1}^{|\Sigma_R|} f(r_j)}$$

Next, the probability of observing an R2R contact event between $r_i$ and $r_j$, if the occurrence is random, can be defined as follows:

$$p(r_i, r_j) = \begin{cases} p(r_i) \cdot p(r_i), & \text{if } i = j \\ p(r_i) \cdot p(r_j) \cdot 2, & \text{if } i \neq j \end{cases}$$

In the case of $i \neq j$, the probability is doubled since the calculation takes two events, i.e., $(r_i, r_j)$ and $(r_j, r_i)$, into account. Then, the standard residual can be defined. First, let $X_{r_i,r_j}$ be a random variable representing the occurrence of an R2R contact event. Since all the interacting events are undirected, let $$X = \sum_{i=1}^{|\Sigma_R|} \sum_{j=1}^{j \leq i} X_{r_i,r_j}$$

be the total number of the R2R-C event. It can be observed that X can be considered as a multinomial distribution, since each R2R contact event $X_{r_i,r_j}$, $1 \leq i \leq |\Sigma_R|$, $1 \leq j \leq i$, is mutually independent. Denoting N as the total number of observed R2R contact events, the standard residual can be defined as:

$$Z_{r_i,r_j} = \frac{X_{r_i,r_j} - E[X_{r_i,r_j}]}{\sqrt{E[X_{r_i,r_j}]}}$$

$$Z_{r_i,r_j} = \frac{X_{r_i,r_j} - N \cdot p(r_i, r_j)}{\sqrt{N \cdot p(r_i, r_j)}}$$

The standard residual is considered to be under normal distribution only when the asymptotic variance of $Z_{r_i,r_j}$ is close to 1. For a more precise analysis, the standard residual has to be adjusted by its variance. The adjusted residual is defined as:

$$s_{r_i,r_j} = \frac{Z_{r_i,r_j}}{\sqrt{\text{Var}(Z_{r_i,r_j})}}$$

Accordingly, at step 102, by converting frequency counts to statistical weights, the R2RCFM may be transformed into a residue-residue adjusted statistical residual matrix (R2RSRM). The numerical value for each entry $(R2RSRM)_{i,j}$ in the R2RSRM corresponds to SR $s_{ri,rj}$. In the R2RSRM, the $j^{th}$ value of the $i^{th}$ row corresponds to the SR of the R2R-I between residue $r^i$ and residue $r^j$. Thus, by treating a row corresponding to a residue (e.g., $r^i$) as a vector with its $j^{th}$ coordinate being the SR of R2R-I between $r^i$ and $r^j$, the R2RSRM may be treated as a vector space referred to as R2R statistical residual vector space (SRV). In other words, the R2RSRM may be considered to define a plurality of statistical residual vectors.

Figure 3B:
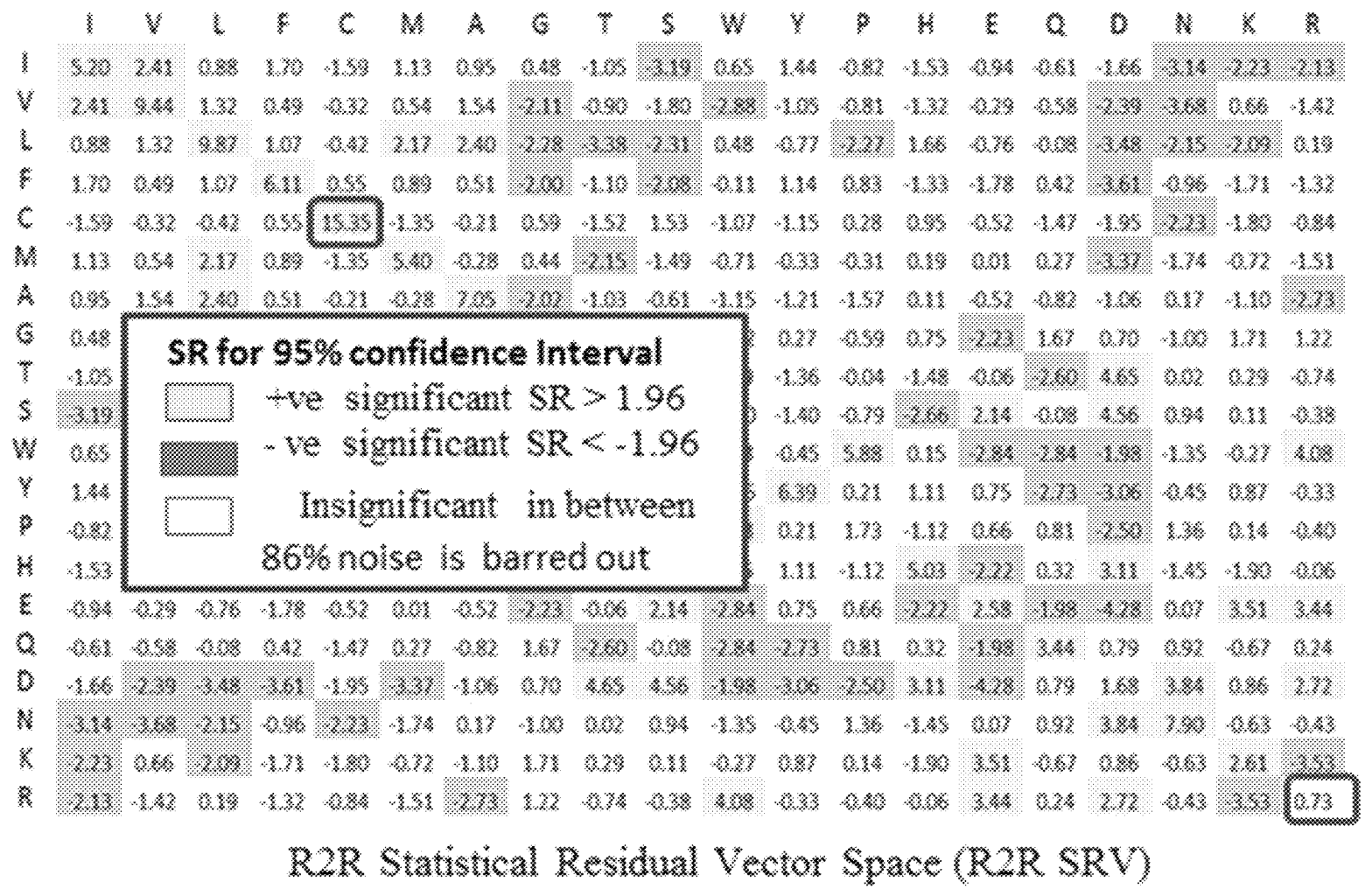

With additional reference to FIG. 3B, an example of the R2RSRM is shown. In this example, the rows and the columns of the R2RSRM correspond to the 20 amino acids. The R2RCRM of FIG. 3B is derived from the R2RCFM of FIG. 3A by the process of transforming the contact frequencies into SRs as described in this document. In this example, the statistical significance threshold θ is set as 1.96 and the SRs in the entries of the R2RSRM are shaded in FIG. 3B if statistically significant for illustrative purposes. As such, this step may include determining for each SR in the R2RSRM if the statistical residue is over a statistical significance threshold or not.

Step 103: Principal Component (PC) Decomposition and Projection

Step 103, includes decomposing the vector of each row in the statistical residual vector space through principal component decomposition and vector projections on principle components to reveal orthogonal interacting functionality through a strength of corresponding coordinates as captured via a variance of principle components.

In accordance with an embodiment, PC decomposition is applied on each of the SRVs of the R2RSRM. The reader is directed to J. Shlens, "*A Tutorial on Principal Component Analysis,*" *ArXiv*, pp. 1-13, 2014, the contents of which are hereby incorporated by reference, for further information on PC decomposition/analysis. Then, residue-vectors in the SRVs are projected onto at least some of the PCs obtained by the PC decomposition to obtain a set of projections of the residue-vectors. In should be appreciated that this step may disentangle the statistical residuals (SRs) to reveal the significance for a specific R2R-I function via their projection onto different principal components.

To facilitate the explanation of the application of PC decomposition, let $q_i=[s_{ri,r1}, \ldots, s_{ri,r|\Sigma R|}]$ be the $i^{th}$ row of SRV S, where S is a $|\Sigma_R| \times |\Sigma_R|$ matrix of the column of row vectors. Each row vector $q_i$ for residue $r_i$ depict $s^{ri,rj}$ as its $j^{th}$ coordinate representing its R2R association with the residue $r_j$. This row vector $q_i$ may be referred to as a residual vector which may be referred to as a $r_i$-vector or r-vector:

$$S = \begin{bmatrix} q_1 \\ q_2 \\ \ldots \\ q_{|\Sigma_R|} \end{bmatrix}$$

In order to disentangle these statistics to reveal different R2R-I functionality, the SRV is decomposed through PC analysis into orthogonal principal components (PCs). Let $m_i$ be the mean row vector of the element-wise means of the row vectors $q_i$, for i=1 to 20. Let $\overline{S}$ be the mean-adjusted matrix of S:

$$\overline{S} = \begin{bmatrix} q_1 - m_1 \\ q_2 - m_2 \\ \ldots \\ q_{|\Sigma_R|} - m_{|\Sigma_R|} \end{bmatrix}$$

In other words, each r-vector in the R2RSRM can be adjusted to obtain a mean-adjusted statistical residual matrix.

The covariance matrix of S' can be computed as:

$$C = \frac{1}{|\Sigma_R|-1} \overline{S}\overline{S}^T,$$

Eigen-decomposition can be performed on C:

$$Cv_i = \tau_i v_i, \text{ for } i=1,2,\ldots,|\Sigma_R|,$$

where $v_i$ is a column eigenvector and $r_i$ is the corresponding eigenvalue.

The eigenvectors once obtained can then be sorted according to the descending order of the eigenvalues, and placed on the matrix V:

$$V=[v_1, v_2, \ldots, v_{|\Sigma_R|}] \text{ such that } \tau_i \geq \tau_{i+1}.$$

These eigenvectors in the matrix V are the principal components, each of which, represent underlying orthogonal components of related molecular function. The functional significance of the projected r-vectors on each principal component can be inferred from the projection of S onto the kth eigenvector:

$$\overline{S}^k = \overline{S} \cdot V_{:,k}$$

$\overline{S}^k$ would be a column vector which represents a weight in the form of an absolute magnitude of its distance from the mean of each residue in the kth PC space. Accordingly, S k can be considered as the projected statistical residual vectors on the kth PC space.

Figure 4A:
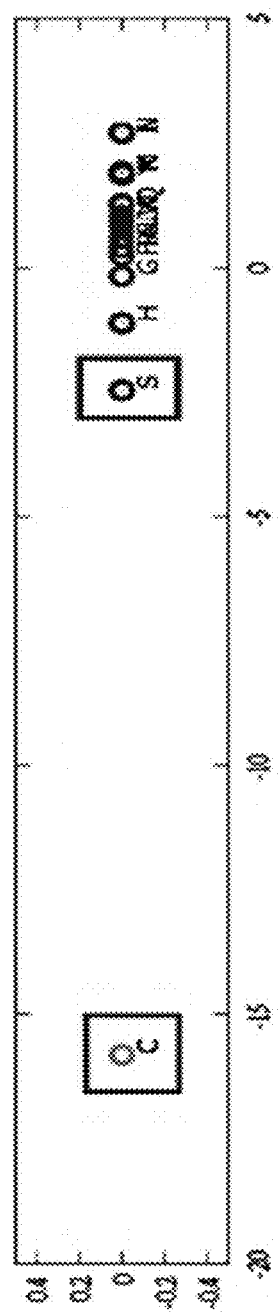

With additional reference to FIG. 4A and FIG. 5A, these figures show projected statistical residual vectors on to a second PC (PC2) axis and a fifth PC (PC5) axis. For the data analyzed in these examples, it was determined by experimental results that the top 6 r-vector projected PCs axis cover about 80% of the data variance and that all of the other r-vector projected PCs axis may not be needed for a useful analysis. For example, to determine the number of PCs to use, we first compute a sum of all eigenvalues as $$U = \sum_{i=1}^{|\Sigma R|} \tau_i,$$

where $\tau_i$ is the i-th eigenvalue sorted in descending order. The percentage of data variance covered is computed by $$\frac{1}{U}\sum_{k=1}^{t} \tau_k.$$

It was found, in this example, that as t=6, the percentage of data variance is almost 80%. Depending on the type of application, the number of project PCs axis determined to be relevant my vary in practical implementations. In FIGS. 4A and 5A there are 20 points, where each point is a projection of an r-vector in the SRV corresponding to second and fifth PC, respectively. In these examples, residues with weights greater than or equal to 1 standard deviation away from the mean of $\overline{S}^k$ are considered to identify the significant coordinates in the SRV $\overline{S}$ that contribute to the eigenvalue of the $k^{th}$ PC as reflected by the weight of them on the PC. For instance, PC2 has a variance of 14.78% and contains a highly distinctive interacting group C and a less distinctive, yet statistically significant, residue S. PC5 has a variance of 7.31% and contains two distinctive groups: R and W, E, D with positive and negative charges respectively. Also, K, near R in PC5, is positively charged.

Step 104: Reprojection of r-Vectors on PC Back to Statistical Residual Vector Space Step 104, comprises re-projecting the vectors projections back to the statistical residual vector space with new vector positions.

In accordance with an embodiment, the projections of the r-vectors on each PC are re-projected onto the SRV, referred to as re-projected statistical residual vector space (RSRV), with a new set of coordinates. To see how much the $k^{th}$ principal component accounts for the interaction of a residue (or a group of residues) interact(s) with other residue(s), the SRV is reconstructed as a new $\overline{S}^{k_1}$ such that the projections of the r-vectors on the $k^{th}$ PC become the r-vectors on $\overline{S}^{k_1}$:

$$\overline{S}^{k'} = \overline{S}^{k} \cdot (V)_{:,k}^T$$

and then element-wise addition on the matrix $\overline{S}^{k_1}$ is performed to obtain a new matrix $S^{k_1}$:

$$S_{k'} = [\overline{S}^{k'}_{:,1} + m_{1,:}, \overline{S}^{k'}_{:,2} + m_{2,:}, \ldots, \overline{S}^{k'}_{:,|\Sigma_R|} + m_{|\Sigma_R|,:}]$$

with a new set of coordinates. The matrix $S^{k_1}$ with a new set of r-vectors depicts the SR of its residue interacting with other residues via its new coordinates as the re-projected SRV (RSRV). The matrix $\overline{S}^{k_1}$ is now a new matrix reflecting the weights in the $k^{th}$ RSRV (RSRVk) according to the $k^{th}$ PC (PCk).

Figure 4B:
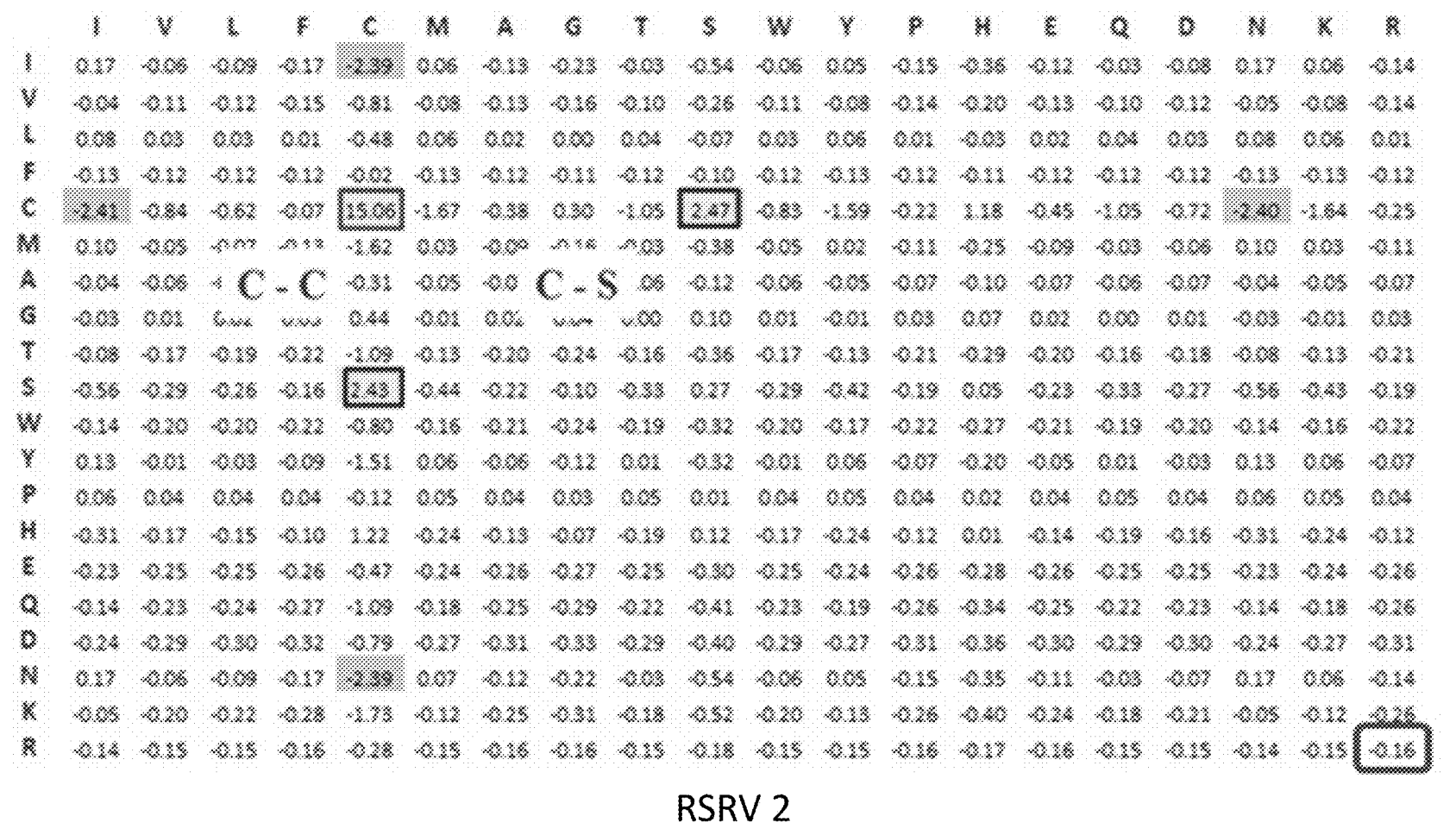
Figure 5B:
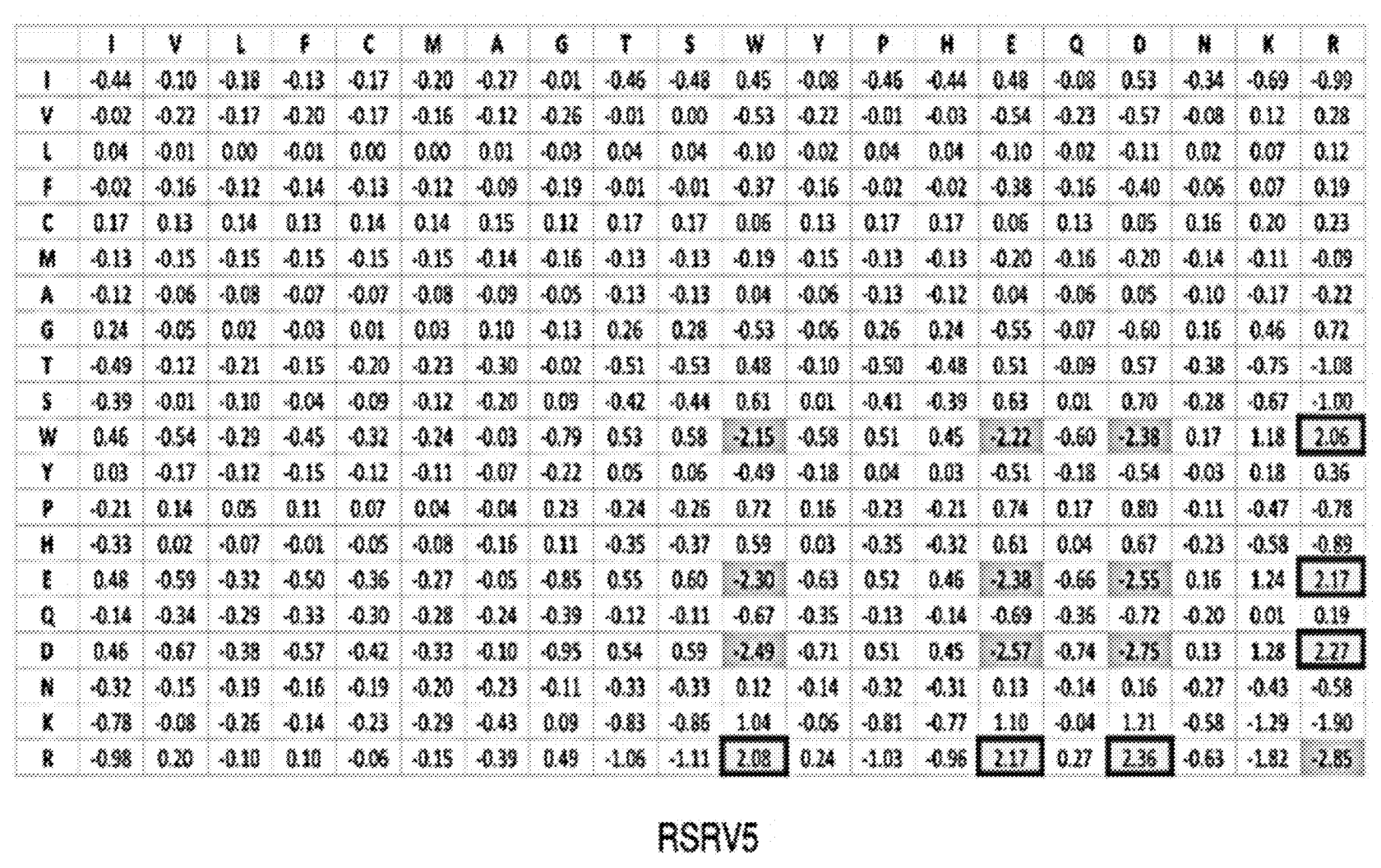

With additional reference to FIGS. 4B and 5B, these figures respectively show the corresponding RSRVs RSRV2 and RSRV5 of the PC2 and PC5 of FIGS. 4A and 4B. For illustration purposes, the RSRVs in FIGS. 4B and 5B show the results of all significant residue interacting functions as elaborated with shading and/or indicator boxes. In RSRV2, the SRs for C-C and C-S coordinates are both positively significant. In RSRV5, for illustration purposes, the residues of opposite charges attract and the residues of same charges repel, and are indicated by the positively and negatively significant SR cells with shading.

It should be appreciated that in FIGS. 4A, 4B, 5A and 5B the R2R the associations masked in the R2RCFM are being disentangled and brought forth in their PCs and RSRVs respectively. As such, applying the methodology of method 10 on residue-residue contact (R2R-C) data may bring forth statistically manifested and functionally specific associations. It may also render a strong statistical and functional base to unveil the deeper knowledge of R2R-I and may improve R2R-I site prediction precision.

The method 10 may also include analyzing the statistical weights in the re-projected statistical residual vector space to reveal specific interacting functions between residues.

The method 10 may also include determining a statistical significance of the specific interaction functions between $r_i$ and $r_j$ for the particular interacting function as reflected in the re-projected statistical residual space.

Step 105: Construction of a R2R-I Predictor

At step 105, a k-dimensional feature vector may be generated for each biomolecule pair ($r_i$, $r_j$). The feature vector may be generating using at least the reprojected vectors in a reprojected statistical residual vector space.

Figures 6A, 6B:
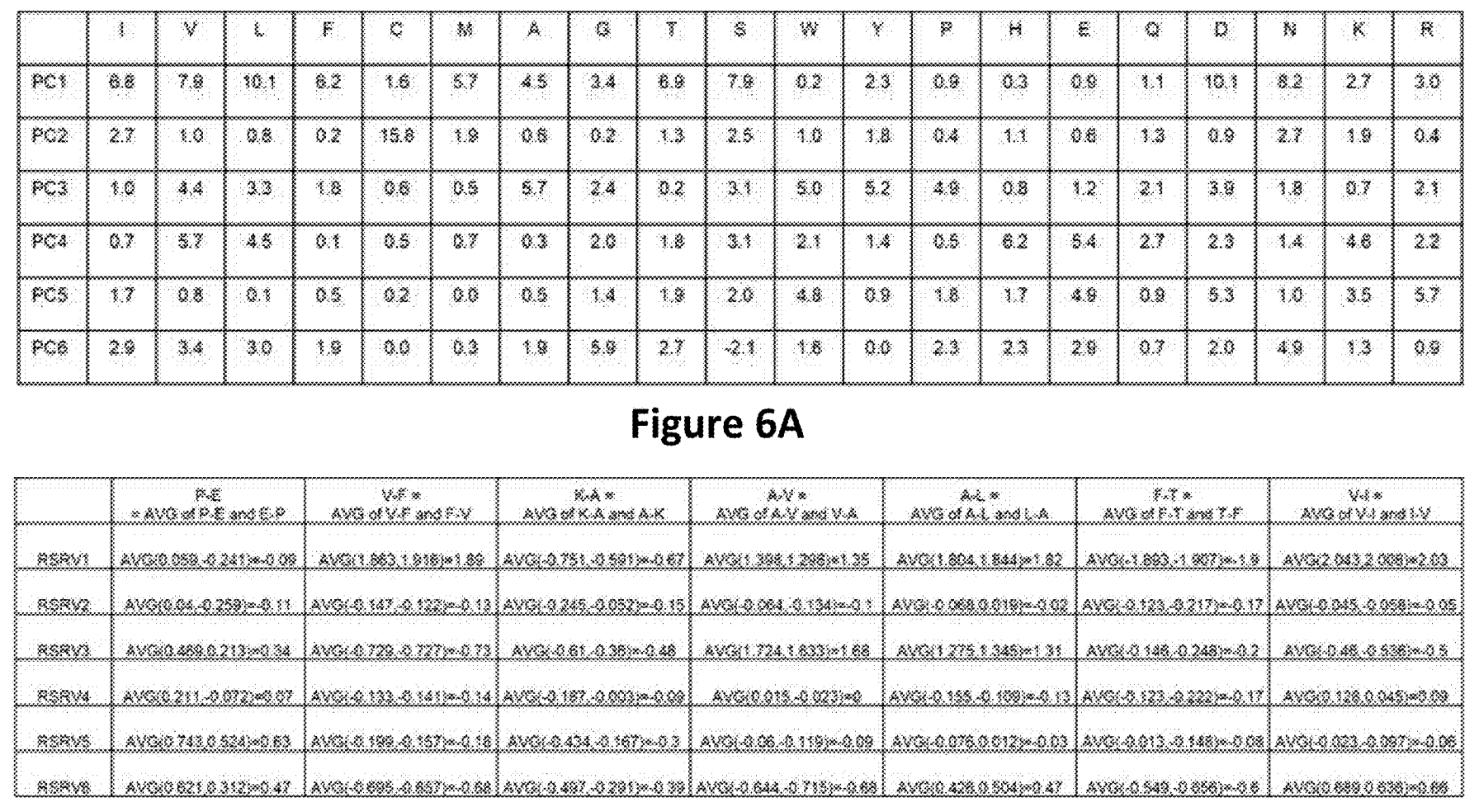
Figure 6C:
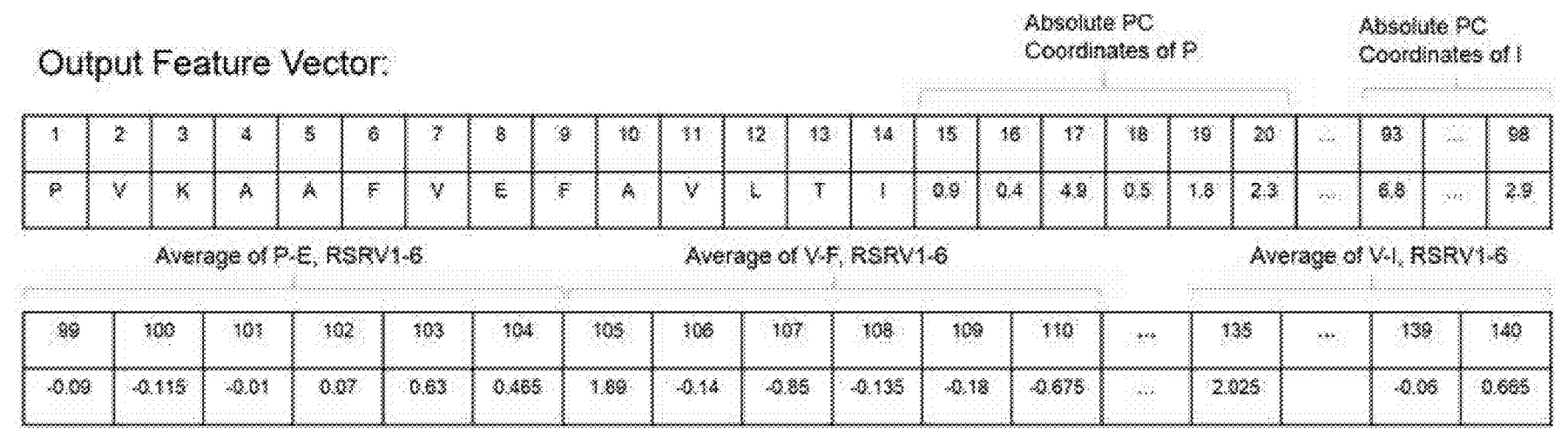

In accordance with an embodiment, the PCs and RSRVs are processed to determine any statistical or functional patterns. Using an indicator threshold, which may be the same value as the distance threshold discussed elsewhere in this document (e.g., 6A), it can be determined if two residues between two protein chains are close or not. For instance, if the distance between two residues between two protein chains are less than the indicator threshold it may be determined that the two residues are close; otherwise, the two residues are considered not close. Under the assumption that two residues are likely to interact if they are close enough in 3D structures, positive examples (i.e., close contact residue pairs) and negative examples (i.e., not close contact residue pairs) may be acquired. For constructing the R2R-I predictor, an R2R-I feature vector may be generated. In this example, the alphabet and PC and RSRV coordinates are used and an example of how to construct the R2R-I predictor is illustrated in FIGS. 6A to 6C. More specifically, FIGS. 6A to 6C illustrate an example of how to construct a feature vector for an R2R-I sample.

FIG. 6A illustrates an example table of the top 6 absolute PC coordinates of the 20 amino acids, which are used in the feature vector. FIG. 6B, illustrates an example table of the re-projected SRV (RSRV) of P-E, V-F, K-A, A-V, A-L, F-T and V-I, which are also used in the feature vector. FIG. 6C illustrates an example of how to construct a feature vector for the target residue pair A-V, with their 3 neighboring residues on both the left and right side added to indicate possible additional interactions concurrent with the residue pair. More specifically, FIG. 6C shows an example of converting an R2R-I sample "PVKAAFV-EFAVLTI" into a 140 dimension feature vector.

In this example of creating the feature vector, in addition to the target residue pair, the 3 neighboring residues from both the left and right side are used. As shown in FIG. 6C, the target residue pair is A-V, and its neighboring residues are added into the target residue pair. Then, the entire residue pair is placed in positions 1-14 of the feature vector, where a missing neighboring residue could be replaced by a '?', and could be handled at the algorithmic level. Next, for each residue on position 1-14, the feature vector is concatenated by the PC projection coordinates of that residue. As shown in FIG. 6C, the positions 15-20 are coordinates of P and, until positions 93-98 of I, are coordinates of I. It should be noted that for each missing residue, the feature vector can be concatenated by 6 zeros. The feature vector is further concatenated by the pairwise re-projected SRVs of PVKAAFV-EFAVLTI. There are in total 7 pairs of re-projected SRVs (RSRVs). They are P-E, V-F, K-A, A-V, A-L, F-T and V-I. For each pair, there are 6 types of RSRVs, which are RSRV1-6. Thus, there are 42 more real values concatenated to the feature vector, for positions 99 to 140. For a missing residue, the feature vector may be concatenated by 6 zeros. In this example, the output feature vector would be of 140 dimensions.

In accordance with an embodiment, given a set of training R2R-I, it would typically not be desirable to use all of them since the number of negative R2R-I outweighs that of positive R2R-I. As such, a set of training samples may be first created to include positive and negative R2R-I at a ratio of 1:19 or any other suitable ratios for any other application. Then, 1200 sets of training bags sampling from the training samples with replacement are created, where each bag contains one-fifth of the original training samples. Each of these 1200 bags is maintained at a balanced ratio between positive and negative R2R-I. Then 400 bags containing only alphabets are set, where the 400 bags containing only absolute values of the PC coordinates, and the 400 bags contain only reprojected SRVs (RSRVs). It should be noted that here the bag numbers 1200 and 400 are for example purposes and may vary in practical implementations. For each bag, a C4.5 decision tree classifier using machine learning software package WEKA 3.7.12 with default parameters except disabling pruning could be trained. To handle missing values, the C4.5 decision tree classifier in WEKA 3.7.12 could consider all branches extending from the corresponding node and select the leaf node with the largest probability. It should be noted that here the C4.5 decision tree classifier and the machine learning software package WEKA 3.7.12 are subjected to changes depending on the implementation. The final R2R-I predictor could be the average probability of these 1200 C4.5 decision tree classifiers.

Step 106: Output of the Predictions

At step 106, the feature vector is inputted into a predictor for each biomolecule pair ($r_i$, $r_j$), and the predictor outputs a likelihood of an interaction site of a corresponding residue pair ($r_i$, $r_j$).

In accordance with an embodiment, an R2R-I predictor between the biosequences is outputted. For example, given any two interacting protein sequences, to predict the interacting residues among them, all possible R2R-I are first enumerated. Then, each of these R2R-I are converted into feature vectors with the R2R-I predictor constructed as an R2R-I prediction score between 0 and 1 inclusively, which may be outputted. In this example, the higher the score, the more likely the residue pair is interacting.

Other suitable forms of outputting the predictions may be possible. For example, graphical indicators such as any of the ones shown in the figures may be used in some embodiments of implementation.

The R2R-I predictor may be outputted to a graphical display and visible to a user via graphical user interface, stored in a database or outputted to any other suitable output or storage device.

The R2R-I predictor may be used in drug discovery, developing new antibodies, and the like.

Benchmark Experiments

A quantitative experiment was conducted to validate the method 10. More specifically, to evaluate the effectiveness of method 10 (also referred to as P2K) in predicting R2R-I sites between two interacting protein sequences, a benchmark experiment was conducted. The benchmark experiment was conducted under leave-one-out-alone cross-validation with comparison to the partner-aware prediction of interacting residues in protein-protein complexes from sequence data (PPiPP) algorithm of S. Ahmad and K. Mizuguchi, "*Partner-aware prediction of interacting residues in protein-protein complexes from sequence data.,*" *PLoS One*, vol. 6, no. 12, p. e29104, January 2011, the contents of which are hereby incorporated by reference, on the protein-protein docking benchmark dataset version 4.0 (DBD 4.0) which contains 176 P2P 3D multi-chain interaction complexes, where DBD 4.0 is provided in H. Hwang, T. Vreven, J. Janin, and Z. Weng, "Protein-protein docking benchmark version 4.0," *Proteins Struct. Funct. Bioinforma.*, vol. 78, no. 15, pp. 3111-3114, 2010, the contents of which are hereby incorporated by reference. Leave-one-out-alone cross validation is a standard procedure to evaluate a machine learning classifier construction (training) algorithm, which is detailed described in Refaeilzadeh, Payam, Lei Tang, and Huan Liu. "*Cross-validation.*" Encyclopedia of database systems. Springer US, 2009. 532-538, the contents of which are hereby incorporated by reference. The following description of leave-one-out-alone cross validation is provided for reference. Assume that there are X samples for training a classifier. X−1 of the samples would be selected for training and the remaining one would be used for testing (evaluating) the trained classifier. The entire process would be repeated X times such that every sample would be used for testing. The overall testing performance would be the average of all the performance obtained in independent testing.

The results of the benchmark experiment are summarized in the tables of FIGS. 7A and 7B. The table of FIG. 7A shows the average accuracy, precision, recall, specificity, F-measure (F1) and AUC achieved by P2K comparing with PPiPP on benchmark dataset DBD 4.0, where the prediction threshold in each case was chosen by maximizing the F-measure. The table of FIG. 7B shows the average accuracy, precision, recall, specificity, F-measure (F1) and AUC achieved by P2K comparing with PPiPP on benchmark dataset DBD 4.0, where in each case only the top 5 positive predictions remained and the other positive predictions were forced to be negative predictions. As shown in these FIG. 7A, P2K achieved a 6.23×better precision and a 4.31×better F-measure than that of PPiPP. In FIG. 7B, on a harder constraint where only the top 5 positive predictions were allowed, P2K achieved a 15.51×better precision and a 19×better F-measure than that of PPiPP.

Figure 8B:
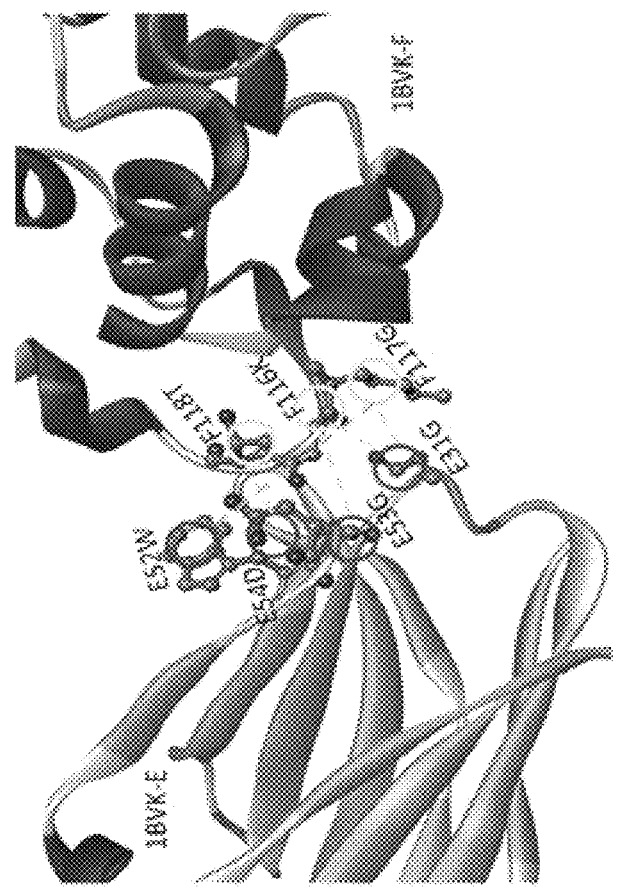
FIGS. 8A and 8B are images of residue-residue interaction site predictions between two example protein sequences.
Figure 8A:
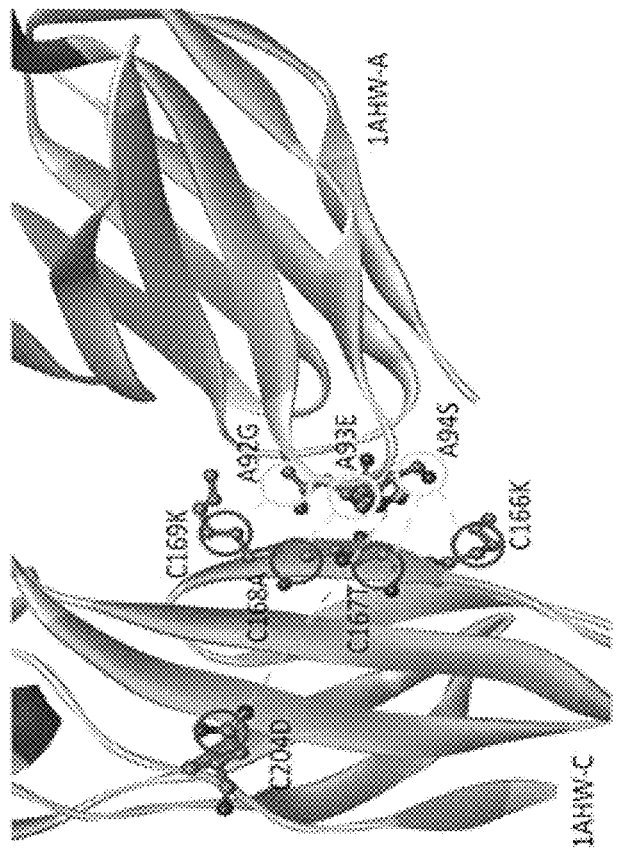

Two individual case studies on the benchmark experiments on DBD 4.0 were also done. The testing complexes are proteins with the PDB having identfiers: 1AHW and 1BVK. 1AHW describes the PPI between Immunoglobilin FAB 5G9 and Tissue Factor (TF). R2R-I occurs in 1AHW-AC and 1AHW-BC. In both cases, P2K outperformed PPiPP while PPiPP had no true positive predictions. 1BVK describes the PPI between hen egg lysozyme and the Fv fragment of a humanized antilysozyme antibody. R2R-I occurs in 1BVK-DF and 1BVK-EF. As shown in FIGS. 7C and 7D respectively, P2K outperformed PPiPP, where the latter had no true positive predictions. The table of FIG. 7C shows accuracy, precision, recall, specificity, F-measure and AUC achieved by P2K comparing with PPiPP on 1AHW-AC for Fold 1 of the Benchmark Dataset DBD 4.0, where in each case only the top 5 positive predictions remained and the other positive predictions were forced to be negative predictions. The table of FIG. 7D shows accuracy, precision, recall, specificity, F-measure and AUC achieved by P2K comparing with PPiPP on 1BVK-EF for Fold 2 of the Benchmark Dataset DBD 4.0, where in each case only the top 5 positive predictions remained and the other positive predictions were forced to be negative predictions. With additional references to FIGS. 8A and 8B examples of R2R-I site prediction between two protein sequences 1AHW-AC (in FIG. 8A) and 1BVK-EF (in FIG. 8B). The top 5 predictions of P2K are shown in FIGS. 8A and 8B, where the 4 true positives and 1 false positive are connected by dash lines. For comparison, none of the top 5 predictions by PPiPP are true positives.

Other Applications

While embodiments are presented in this document to derive, disentangle and transform from R2R-C data the statistical R2R associations corresponding to individual functional components and use them to determine R2R-I site predictions between two interacting protein sequences, it should be appreciated that it is for example purposes and other applications are possible in other embodiments.

It should be appreciated that P2K may have important applications in drug discovery by assisting the design of antibodies to bind at R2R-I sites. The example of predicting interaction sites between hen egg lysozyme and the Fv fragment of a humanized antilysozyme antibody could be applied to identify R2R-I sites between therapeutic monoclonal antibodies and human endogenous retroviruses, emerging as novel tumor-associated antigens. Hence it should be appreciated that P2K can also be applied in predicting the Protein-Antibody interaction sites between two sequences.

It should be noted that P2K has not made any specific assumptions that the input sequence be a protein sequence. In fact, P2K could be applied to predict other biosequence interaction sites such as Protein-DNA interaction sites, Protein-RNA interaction sites, RNA-RNA interaction sites, provided that the alphabet set $\Sigma_R$ and the type of accumulative 3D structures change accordingly.

In a broader context, P2K can be extended to sequences beyond biosequences. Given two non-biosequences, P2K can thus be applied in this broader type of application by defining the alphabet set $\Sigma_R$, how two alphabets interact or associate in the two non biosequences respectively, and provide training examples of the interaction/association. Therefore, the P2K methodology may be used to extract deep disentangled, quantifiable and verifiable knowledge from a wide variety of biosequence and non-biosequence data sets. The section entitled "Attribute Value Association Algorithm (AVAA)" further discusses an extension of P2K methodology to extended the analysis beyond biosequences.

Attribute Value Association Algorithm (AVAA)

Figure 9:
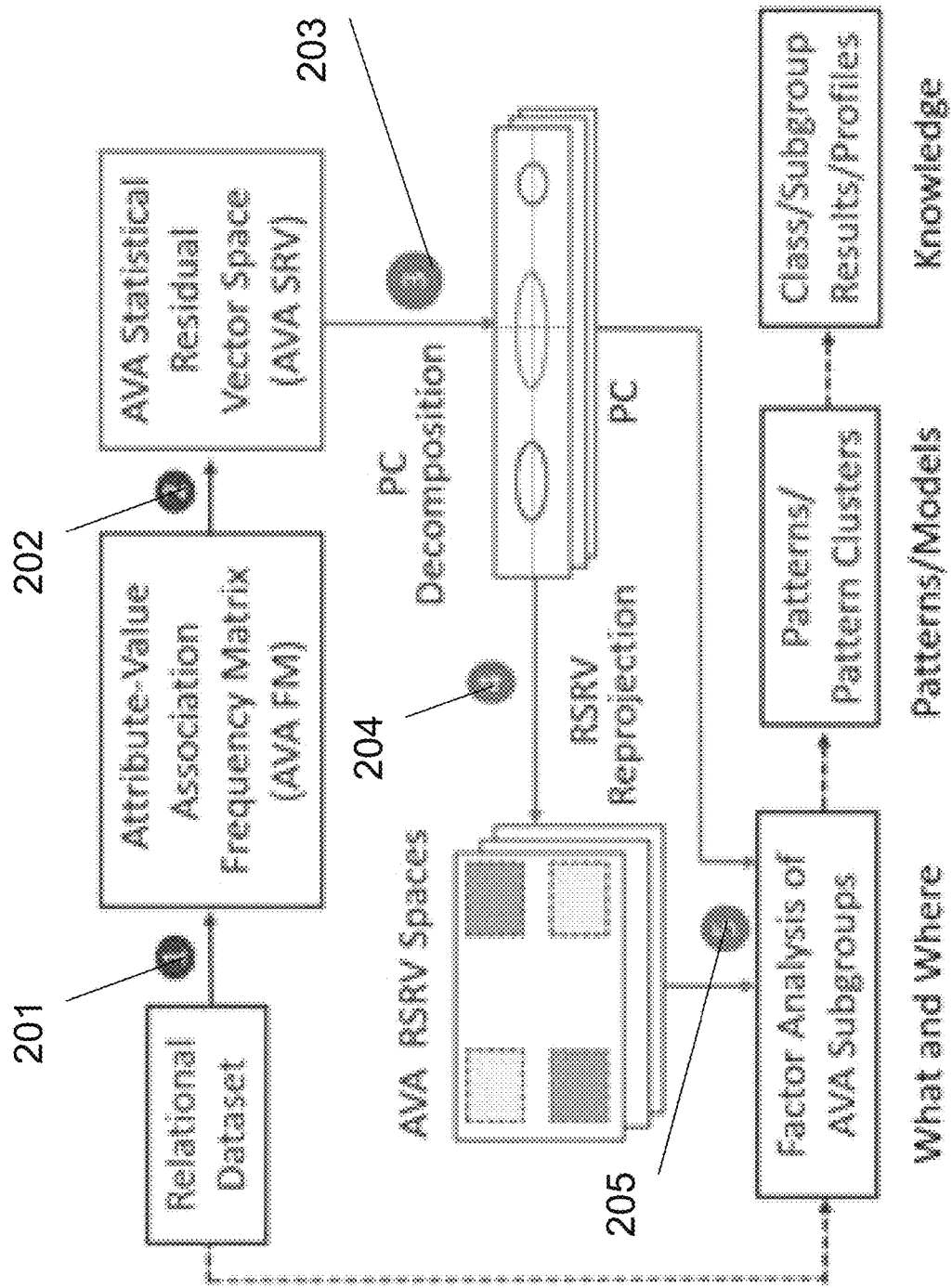
FIG. 9 is a schematic overview for determining attribute-value association from relational data in accordance with an embodiment.

With reference now to FIG. 9, a schematic overview of an algorithm referred herein as the attribute value association algorithm (AVAA) is provided. In accordance with an embodiment, the AVAA may be used to discover from relational datasets subtle associations affected by certain underlying governing factors. In general terms, given a relational dataset, the AVAA functions as follows: a) first obtain an attribute value association frequency matrix (AVA FM) where each entry is a frequency of co-occurrences of an attribute value association (AVA) of two attributes among all samples; b) obtain an AVA statistical residual vector space (SRV) in the form of a matrix by converting each frequency in the AVA FM into a statistical residual in SRV accounting for the deviation of the observe frequency against the expected frequency if that AVA is a random happening; c) disentangle this SRV matrix, by principal component (PC) decomposition and re-projection of a-vector projections on each PC back to a new SRV to possibly reveal further information that may be governed by various inherent factors.

AVAA works on an AVA level. In other words, AVAA goes beyond a sample vector level, to the AVA level. It represents the AVA by their statistical residuals (SR) to amplify their statistical strength and to minimize the sensitivity of attribute scaling. AVAA applies PCA through disentangling SRV followed by re-projection to obtain RSRVs governed by different factors. Each RSRV contains AVAs associating with a hidden factor captured in its corresponding PC. AVAA leverages the transformed re-projected SRV (RSRV), obtained via PC re-projection, to render explicit interpretation for different AVA groups. From the disentangled SR spaces, specific governing factors related to the AVA are revealed to provide an enhanced understanding of the inherent relation of classes/subgroups as well as their identification. In other words, AVAA disentangles, through PC decomposition, the SR, and reveals different AVA groups governed by different underlying factors, through PC a-vector re-projection onto RSRV.

Figure 10:
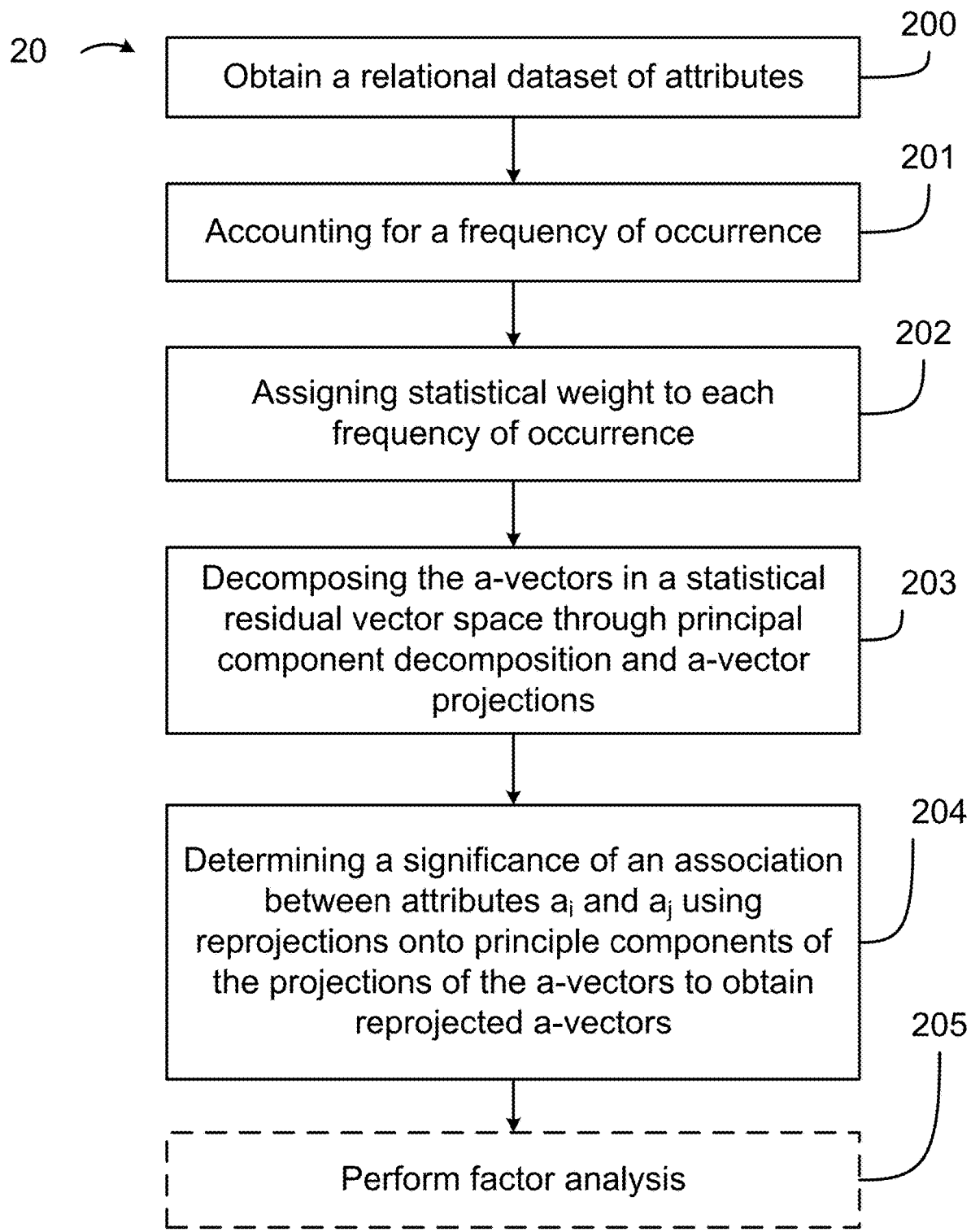
FIG. 10 is a flowchart illustrating an example method for determining attribute-value associations from relational data in accordance with an embodiment.

With additional reference to FIG. 10, there is shown a flowchart illustrating an example method 20 for implementing the AVAA.

Step 200: Data Acquisition and Pre-Processing

At step 200, a plurality of pairs of attributes $(a_i, a_j)$ from a relational dataset are obtained.

In accordance with an embodiment, a relational dataset is obtained that includes relational data. The relational dataset may be obtained from a database and/or any other suitable computer readable medium. The relational data set may be defined as a relational dataset R, which may be a set of N-tuples of mixed-mode data with the following characteristics:

1. Every tuple in R is described by N attributes, denoted as $A = \{A_1, \ldots A_n \ldots A_N\}$.
2. Each attribute $A_n$ can assume a continuous numerical value or a categorical value.
   a. For continuous attributes, $A_n$ is partitioned into I bins, by transforming the original numerical values of $A_n$ into interval event values, denoted as $A_n = \{A_n^i | i=1, \ldots I\}$.
   b. For categorical attributes, $A_n$ contains J values, denoted as $A_n = \{A_n^j | j=1, \ldots J\}$.

After transforming the mixed-mode dataset into event-value dataset, all the values of each attribute $A_n$ can be denoted as $E = \{e_1, e_2, \ldots e_I\}$, where I represents the total number of the attribute's event-values.

Step 201: Determining a Frequency of Occurrence

At step 201, comprises accounting for a frequency of occurrence of every pair of attribute values $(a_i, a_j)$ in the relational dataset.

In accordance with an embodiment, the relational dataset is processed to partition attributes with real value into bins and an AVA frequency matrix (AVA FM) is constructed from the AVA frequency obtained from the relational dataset. An inductive method is provided to obtain the AVA FM. The AVA FM is a matrix of frequency count of an AVA between two attribute values (AVs). For example, let $A_n^i$ be the $i^{th}$ value of the $n^{th}$ attribute and $A_{n'}^j$, the $j^{th}$ value of the $n'^{th}$ attribute (n≠n'). For instance, the AVA FM may be denoted as $FM(A_n^i \leftrightarrow A_{n'}^j)$.

Step 202: Conversion of Frequency Matrix into Standard Residual Vector Space

Step 202, includes determining a statistical weight for each frequency of occurrence as a function of a deviation of the frequency of occurrence from an expected frequency if a given association is a random happening to obtain a statistical residual frequency matrix, wherein the statistical residual frequency matrix is considered as a statistical residual vector space such that each row is an attribute-value vector (a-vector) having coordinates that are statistical residuals of a given attribute value associating with other attribute values For example, a statistical weight is obtained for each frequency of occurrence as a function of a deviation of the frequency of occurrence from an expected frequency if the association is a random happening to obtain a statistical residual frequency table, wherein the statistical residual frequency table is considered as a statistical residual vector space such that each row is an a-vector (attribute-value vector) representing that given attribute value associating with other attribute values as a coordinates.

In accordance with an embodiment, the AVA FM is converted into another matrix by replacing each AVA frequency in the AVA FM with its SR. In general terms, each SR accounts for the deviation of the frequency of the AVA occurrences from random occurrences of the AVA. This matrix of SRs is treated as a vector space, referred to as SRV, such that each row is taken as a row vector referred to as an attribute value (AV) vector (a-vector). The coordinates of the a-vector represent the SR of the AV associated with another AV represented by the column a-vector.

Figure 11:
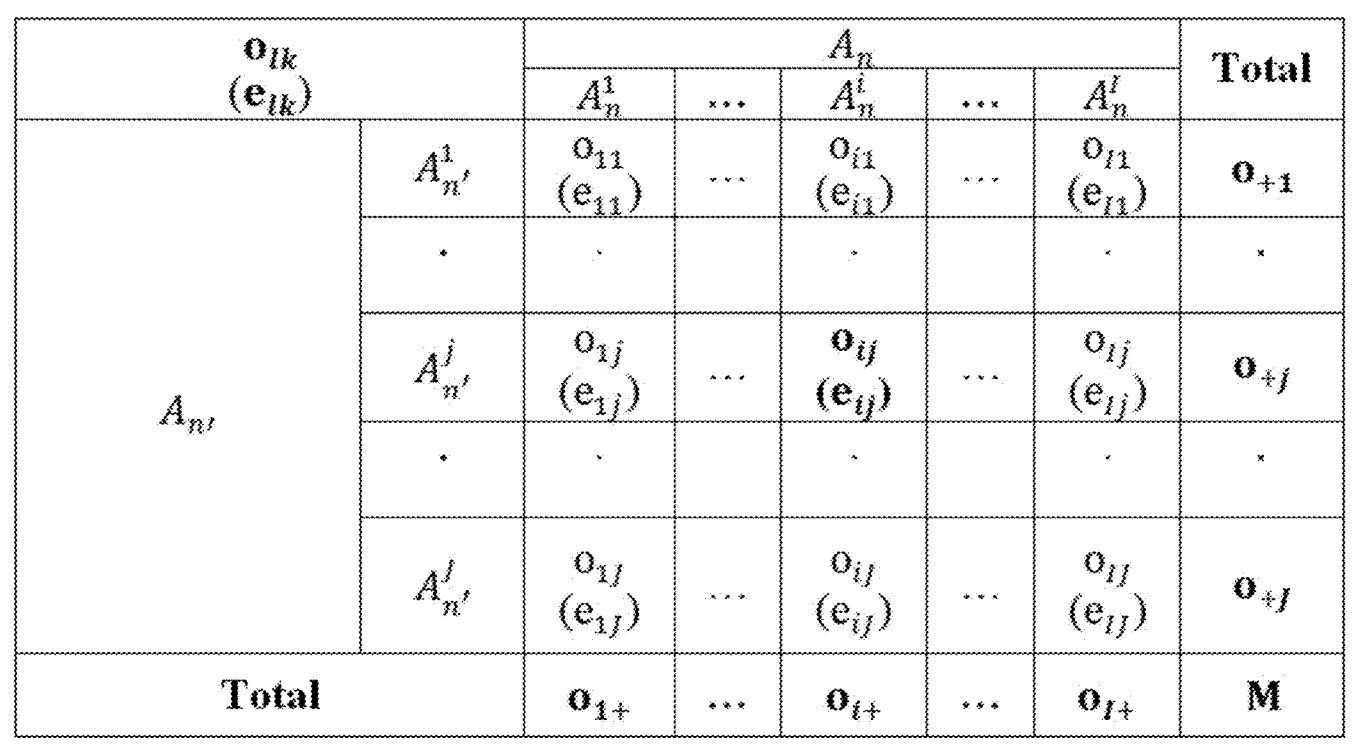

To assist the reader in visualizing how the AVA FM is converted into an SRV, FIG. 11 illustrates a table formatted with J rows and I columns, where I is the total number of states of A n and J is the total number of states of $A_{n'}$.

To obtain statistically significant information from R, the AVA FM is transformed into a statistical residual matrix by transforming each AVA frequency into an SR through equation (2) on the pair of the observed frequency and its expected one. SR measures the deviation of the observed frequency of the AVA from its default model if it is a random association instead. In the table of FIG. 11, $o_{ij}$ represents the total number of occurrences when $A_n = A_n^j$ and $A_n = A_n^i$;

$$e_{ij} = \frac{1}{M} \sum_{u=1}^{J} o_{iu} \sum_{u=1}^{I} o_{uj}$$

where $$\sum_{u=1}^{J} o_{iu}$$

represents the total number of counts when $A_n = A_n^j$; and $$\sum_{u=1}^{I} o_{uj}$$

represents that when $A_n = A_n^i$ and M is the number of records. Hence, the value of $FM(A_n^i \leftrightarrow A_{n'}^j)$ can be obtained by the following equation:

$$FM(A_n^i \leftrightarrow A_{n'}^j) = \frac{o_{ij}}{M} \quad (1)$$

By using the same example as above, given $o_{ij}$ and $e_{ij}$, there is an interest in determining whether $o_{ij}$ is significantly different from $e_{ij}$. To scale the difference, the SR, as expressed below in equation (2) may be used:

$$SR(A_n^i \leftrightarrow A_{n'}^j)(SR_{ij}) = \frac{o_{ij} - e_{ij}}{\sqrt{e_{ij}}} \quad (2)$$

The SR value can reveal the statistical significance of an AVA. At the confidence level of 95%, if the SR >1.96, the discovered AVA is "+ve significant"; the discovered AVA is "−ve significant" if the SR<−1.96; and the discovered AVA is irrelevant or random if the SR is between −1.96 and 1.96. In the less prominent RSRVs, the confidence level could be lowered to 80% since the frequencies of their AVAs could be rarer. Accordingly, the confidence level may vary from the example values given in this document depending on the practical implementation.

The AVA standard residual vector space (SRV) is a vector space such that the $j^{th}$ coordinates of its $i^{th}$ row vector $SRV_{A_n^i}$ is the SR derived from the observed frequency that $A_n^i$ is associated with $A_n^i$. Hence, SRV can be expressed as a set of row vectors:

$$SRV = \{SRV_{A_1^1}, SRV_{A_1^2}, \ldots, SRV_{A_N^I}\},$$

where N is the total number of attributes, and I is the total event-values of an attribute $A_n$. An a-vector is denoted as $SRV_{A_n^i} = \{SR(A_n^i \chi A_n^j), \ldots SR(A_n^i \leftrightarrow A_n^j), \ldots SR(A_n^{ni} \leftrightarrow A_n^j)\}$, where $SR(A_n^i \leftrightarrow A_n^j)$ represents the standard residual for AVA $(A_n^i \leftrightarrow A_n^j)$, and $A_n^i$ represents the $i^{th}$ AV in attribute $A_n$ and $A_n^j$ represents the $j^{th}$ AV in attribute $A_{n'}$ (n≠n').

Step 203: Principal Component Analysis

At step 203, the a-vectors in the statistical residual vector space are decomposed through principal component decomposition and a-vector projections to reveal orthogonal interacting functionality through a strength of corresponding coordinates as captured via a variance of principle components.

Although the SR may reveal the significance of an AVA, subtle associations could still be entangled and masked. As such, a principal component analysis (PCA) is used to disentangle the AVA SR. In accordance with an embodiment, the PCA is conducted on the SRV to obtain principal components (PCs) via PC decomposition. After applying PC decomposition on the SRV, the principal components (PCs) are ranked according to their variance and/or their eigenvalues.

At this step, the AVA standard residual vector space (SRV) may be first considered as a vector space by treating each row in it as a vector corresponding to its labeled AV, i.e. as an AV-vector (a-vector), such that the coordinates of which represent the SR of that AV associating with other AVs represented by the column a-vectors. Thus, the $j^{th}$ coordinate of the $i^{th}$ row vector is the SR of the $i^{th}$ AV associating with the $j^{th}$ AV.

In PC decomposition the PCs are a set of k PCs, denoted as PC={$PC_1, PC_2, \ldots PC_k$}, where $PC_k$ is a set of projections of the a-vectors from SRV, denoted as $PC_k = \{PC_k(A_n^i) | n=1, 2, \ldots N, i=1, \ldots I\}$, where N is the total number of all attributes and I is the number of states of each attribute $A_n$.

The PC decomposition/analysis may be performed in a similar manner as discussed elsewhere in this document.

Step 204: Reprojection of a-vectors in PC to Statistical Residual Vector Space (RSRV)

Step 204, includes determining a significance of an association between the attribute values ai and aj using reprojections of the a-vectors on the principle components onto a reprojected statistical residual vector space to obtain new coordinates for the a-vectors reflecting statistical residues of attribute value associations as captured in corresponding principal components For example, a significance of an association between a, and a, is determined using reprojections onto the principle components of the projections of the a-vectors to obtain reprojected a-vectors in the corresponding RSRVs.

It should be appreciated that while reference may be made to reprojected statistical residual vector (RSRV) it may include reference to multiple spaces.

In accordance with an embodiment, the projections of all of the a-vectors on each PC are re-projected back to an SRV to obtain re-projected SRV (RSRV). In general, the RSRV corresponds to a new transformed position rendering new AV SR values with orthogonal functionality captured in the corresponding PC.

It should be appreciated that a-vectors can be projected on to each principal component. The distinct projection(s) of the a-vectors may be identified and the clusters at a great distance from the mean of the PC axis may also be identified. The coordinates of these a-vectors in significant PCs may have a strong associations or a strong presence captured by the orthogonal PC spaces of large variance. Accordingly, distinctiveness, such as deviation from the mean, may indicate certain strong and distinctive associations of the a-vectors with others. Hence, the new positions of a-vector projections on the PC axis when transformed back to the SRV represent the a-vectors with a new set of coordinates reflecting the SRs of their AV associating with other AVs captured in that PC space—this SRV may be referred to as the RSRV corresponding to that PC. Accordingly, the notation of RSRV k as corresponding to $PC_k$ may be used.

The RSRV, which is the SRV containing the transformed position of a-vectors on the PC space may be denoted by equation (3):

$$RSRV_k = SRV \cdot PC_k \cdot PC_k^T \qquad (3)$$

It is also noted that since in the disentangled RSRVs, the AVA corresponding to a PC of lower eigenvalue could be rarer. Hence, a lower confidence level may be adopted to assess the less dominating yet distinct AVAs in the disentangled RSRVs, say between 95% and 80% (e.g., as shown in FIG. 19D).

To reiterate aspects of steps 203 and 204, PCA uses an orthogonal transformation to transform a set of possible correlated variables into a set of linear uncorrelated variables known as PCs. In the transformation, the first PC has the largest possible variance which generally corresponds to the largest variability in the data. Each succeeding PC in turn has the next highest variance under the constraint that it is orthogonal to the preceding PC. In accordance with an embodiment, as each row a-vector represents an AV associating with other AVs as its coordinate, the PC transformation brings out in the PC the highest variance of the a-vectors with high SR coordinate values and outputs them at the far ends from the mean. At the surface, it may not be appreciated why an a-vector is significant. However, when viewed in the RSRV, it should be appreciated that the coordinate(s) contributing to its high variance on the PC. In general, PCA is sensitive to the relative scaling of the original variables, masking their distinctiveness. Hence, by converting the AVA FM into SRV with uniform SR scale and statistical weights, AVAA may utilizes the statistical strength and functional decomposition to reveal more stable, subtle yet significant associations that might be masked in the original frequency space. Hence, the AVAs discovered and disentangled may be more distinct, stable and specific as manifested in the RSRVs.

Step 205: Factor Analysis

At step 205, from the RSRVs, a factor analysis may be conducted to rank and group the significant SR of AVA according to the confidence interval. Realizing that some of the minor governing factors may be rarer, it is appreciated that the lower SR thresholds could be used to obtain deeper and rarer knowledge inherent in the data, revealing classes and/or subgroups under the influence of obscured underlying factors.

The method 20 may further include using significant residuals in each re-projected statistical residual space to reveal disentangled attribute value associations to determine attribute value subgroups governed by underlying factors captured by principal component analysis without reliance on explicit prior knowledge.

Time Complexity Analysis

A time complexity analysis of AVAA suggests two major parts: the computation of SRV and the PCD process.

The SRV computation: Assume that a N×M dataset is the input data, where N is the attribute number and M the record number, the time complexity is $O(MN^2)$. Then, the original data is transformed into an nN×nN matrix, where nN is the number of attribute values.

PCA: It is applied to the SRV, an nN×nN matrix, to obtain eigenvalues and eigenvectors. PCA is composed of two steps. Step 1 is the computation of covariance matrix and its time complexity would be $O((nN)^3)$, where nN is the number of attribute values. Step 2 is the eigenvector decomposition and its time complexity is $O((nN)^3)$. Hence, the overall complexity of AVAA would be $O(MN^2 + 2(nN)^3)$.

For big data applications, the main task of SRV is the "word count". Hence, the time complexity can be accelerated to $N^2$ using a distributed implementation of stochastic PCA to reduce the AVAA complexity to $O(N^2 + (nN)^2 d)$ where d is the number of principle components expected to obtain.

Experimental Results and Analysis

Experiments on synthetic data were conducted to validate the functionality of AVAA and to compare its AVA identification rate with its counterparts. To show that AVAA can handle both categorical and numerical data and reveal subtle yet explainable associations, a real-world clinical mixed-mode data was taken from the UCI dataset of A. Asuncion and D. J. Newman, "*UCI Machine Learning Repository,*" *University of California Irvine School of Information*, vol. 2008. p. 0, 2007, the contents of which are hereby incorporated by reference.

Experimental Result of AVAA for Synthetic Dataset 1:

A first set of synthetic data was designed to demonstrate how patterns entangled in a relational datasets, even within a subgroup of samples, could be disentangled to reveal different AVA groups; as well as how each entangled patterns could be located in the samples. FIG. 12 shows how this synthetic dataset is organized to illustrate the ideas of pattern entanglement and later their disentanglement via AVAA and to reveal the SR of AVAs in RSRVs as well as to map them back to the relational dataset.

In this example, a 400×9 matrix is generated made up of characters A, B and C which were randomly distributed via a pseudo random number generator. This matrix represents the background noise of a relational table with 400 samples and 9 attributes. The patterns of three different classes 1, 2 and 3 ($C_1$, $C_2$, and $C_3$) are embedded with the AVs made up the patterns in the boxes (C-boxes) $C_1$, $C_2$, and $C_3$ shown in FIG. 12. The embedding scheme follows the row numbers as specified in column 1 of FIG. 12. The first, third and fifth rows in the FIG. 12 shows the distinct patterns of $C_1$, $C_2$, and $C_3$ through their respective C-boxes. The second and the fourth rows represent the entangled multiple patterns shown by the C-boxes. The last row represents a 2-value patterns of a weak $C_3$. The information and noise ratio of the data set is approximately 41%.

FIG. 13 illustrates several examples of the discovered patterns as displayed in the N-tuple of the relational data set. It illustrates how each correlated significant AVA group is able to reveal the governing and entangled patterns on the tuples as observed in row 3 and 4 of FIG. 13 respectively through the C-boxes. This illustrates how AVAA may reveal multiple patterns inherent in the data to unveil the buried knowledge.

Figures 14A, 14B, 14C, 14D:
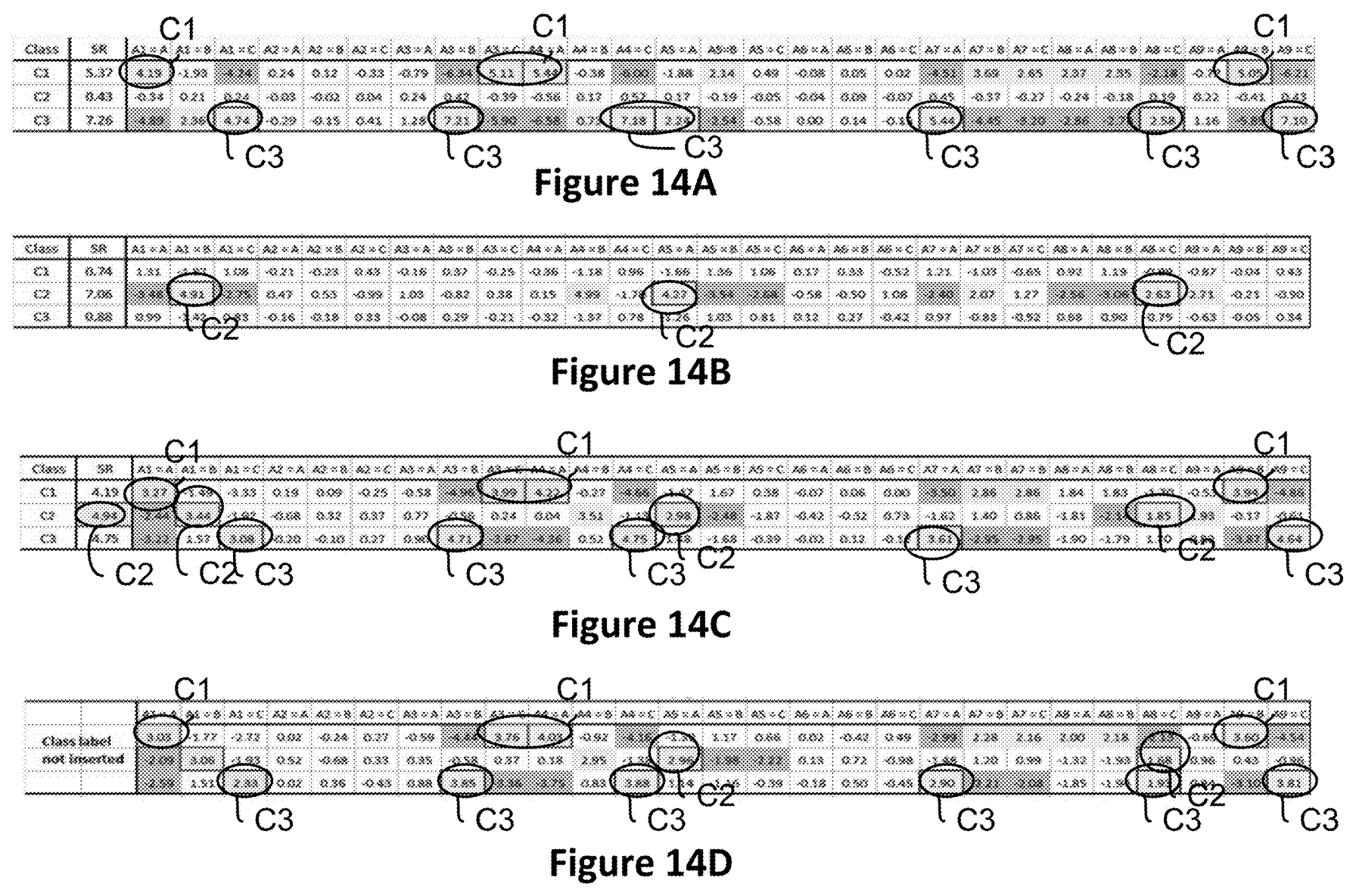

Referring now to FIGS. 14A to 14D, several examples of the experimental result on this synthetic dataset are shown. FIG. 14A illustrates AVA groups associating to C1 and C3 in RSRV1. FIG. 14B illustrates AVA group associating to C2 in RSRV2. FIG. 14C illustrates AVA group associating to class with given class label. FIG. 13D illustrates AVA group associate to classes without class labels.

FIGS. 14A and 14B show that AVA disentanglement does bring forth much succinct and distinct correlated AVA groups in different RSRVs ($RSRV_1$ and $RSRV_2$). It can be observed that the most statistically significant AVAs such as those of $C_1$ and $C_3$ with strong (SR) in the C-boxes in $RSRV_1$. In FIG. 14B it is noted that significant pattern associating with $C_3$ in $RSRV_2$. $RSRV_1$ brings out two diametric groups as revealed by the C-boxes. $RSRV_2$ brings out only a single group. When class labels were given, it is observed in FIG. 14C that a strong association with a group of AVAs with high SR in $RSRV_1$. When class labels were not included in the dataset, AVAA was still able to bring out the AVA groups associating with different classes or subgroups as shown in FIG. 14D, if the intrinsic association to subgroups exist. Note that the corresponding SR magnitudes in FIGS. 14C and 14D are very close. It shows that AVAA may be effective in revealing deep knowledge and providing direct insight without reliance on explicit prior knowledge.

Comparison with Other Algorithms

A performance comparison was done between the SRV and AVAA methods and the QuantMiner (Freq-1, Freq-2), or simply Frequent Pattern Mining (FPM) algorithm, of A. Salleb-Aouissi, C. Vrain, C. Nortet, X. R. Kong, V. Rathod, and D. Cassard, "*QuantMiner for Mining Quantitative Association Rules,*" *J. Mach. Learn. Res.*, vol. 14, pp. 3153-3157, 2013, the contents of which are hereby incorporated by reference.

QuantMiner is an association rule mining system supporting even quantitative rules. By setting different support and confidence value different AVAs can be discovered. Thus, for Freq-1, the threshold was set as: $\sigma_{supp}=35\%$, $\sigma_{conf}=60\%$ (high); and for Freq-2, the threshold was set as: $\sigma_{supp}=10\%$, $\sigma_{conf}=40\%$ (low) where $\sigma_{supp}(A_n^i \leftrightarrow A_{n'}^j)=Pr(A_n^i, A_{n'}^j)$ and $$\sigma_{conf}(A_n^i \leftrightarrow A_{n'}^j) = \frac{Pr(A_n^i A_{n'}^j)}{Pr(A_n^i)}.$$

The SRV method uses only the standard residual (SR) values (Eqn. (2)) to assess the discovered AVAs between all AV pairs for significant AVA identification (with SR >1.96).

AVAA uses the SRs in RSRVs to identify statistically distinct and significant AVAs. Due to the disentanglement, the statistics of the disentangled AVAs are usually weaker. Hence, we set a rule with lower SR threshold for RSRVs corresponding to PCs with lower variance (e.g., over 80% confidence intervals). It is noticed that the SR values of significant AVAs still stand out prominently from the noise background.

For the purpose of performance evaluation of the synthetic experiments and due to that the AVAs are pre-inserted, an identification rate (IR) is used to evaluate how accurate are the correct inserted AVAs (include hidden/entangled ones) discovered. IR is defined as:

$$IR = \frac{TP + TN}{N}, \qquad (4)$$

where N is the total number of AVAs; TP is a true positive rate, which measures the proportion of positives of the correctly identified pre-defined AVAs; and TN is the true negative rate, which measures the proportion of negatives that are correctly identified based on the pre-defined AVAs.

Experimental Result of AVAA for Synthetic Dataset 2:

The second synthetic data set is designed to find out how well the AVAA is in discovering a small set of hidden AVAs while the majority of them are pertaining to the other class. In this experiment, a dataset was generated containing 60 attributes $a_1, a_2, \ldots a_{60}$ with 500 records pertaining to two different classes $C_1$, and $C_2$, e.g., representing normal and cancerous patients, 250 for each.

For $C_1$ (Cancer), 50 strong AVAs were inserted between class label and all the other 50 attributes, say $v_1, v_2, \ldots, v_i, \ldots v_{50}$. The pattern for $C_1$ was constructed by assigning to $v_i$ attribute the value of 0 or 1 randomly. To allow noise, the values of the remaining 10 attributes are and 1 randomly distributed.

For $C_2$ (Normal), in order to make its pattern different from that of $C_1$, 50 strong AVAs were inserted between class label and all the other 50 attributes $v_1, v_2, \ldots v_i, \ldots v_{50}$ such that if for $C_1$ $v_i=0$, then for $C_2$ $v_i=1$ and the values for the other 10 attributes are 0 or 1 randomly distributed. For convenience, in $C_2$, the notation of $-v_i$ was used to represent its $i^{th}$ attribute corresponding to attribute $v_i$ for $C_1$ In this example, a small group, referred to as special cancerous group (CS), still labeled as $C_1$ is considered. For this special class, 34 hidden AVAs were randomly inserted with the value of $v_i$ same as $C_1$ while other attributes were same with $C_2$. The number of records of CS was increased from 10% (50 records) to 100% (500 records).

With this set of synthetic dataset, it was desirable to find out whether AVAA can discover the hidden AVAs from the anomaly. By only consider the AVA between class labels and AVs, it was found that there are 50 strong AVAs between $C_1$ and the AVs ($v_i$); 50 strong AVAs between C2 and the AVs ($-v_i$); and 34 hidden AVAs between $C_1$ and selected AVs ($-v_i$). The IR comparison result using different algorithms are given in FIG. 16.

From the experimental results, the following conclusions were made:
a. The performance of FP (Freq-1 and Freq-2) depends on the thresholds set. The high threshold can guarantee the significance of the discovered AVAs, yet difficult to reveal hidden AVAs when their sample size is small.
b. For the low threshold setting, FPM can reveal strong patterns first but not the hidden AVAs that well (83%), yet when more records containing hidden AVAs are added (after 70%) FPM identifies all of them as well.
c. AVAA outperforms other algorithms since it can discover hidden AVAs even when only 40% of them are inserted.
d. AVAA may discover more hidden patterns corresponding to different functional groups in different RSRVs.

A further comparison was done to compared the IR result using 1) FP with different thresholds; 2) SR and 3) AVAA, to test if AVAA could still discover both strong AVAs and hidden AVAs originally embedded in the data when different levels of noise of 50% to 200% are added. The results are shown in the table of FIG. 17. It can be concluded from table in FIG. 17, that AVAA can handle noise better than FP and SR vectors.

Experiment on Clinical Data

Statlog (Heart) Data was taken from UCI dataset to validate and evaluate the performance of AVAA. The UCI dataset is a mixed-mode relational dataset and is described further in FIG. 18. Class labels were introduced in the AVA FM. For clinical data used for diagnosis, it was expected that a strong dominating a-vectors on opposite sides of the PC with largest variance such as PC1 (FIGS. 15A and 15B) with strong AVA in both SRV and RSRV1. It was observed that strong SRs associating with both $C_1$ and $C_2$ (in FIG. 15C). Note that the SR of the same AVs for the two different sets of diametrically different a-vectors for $C_1$ and $C_2$ are with opposite (positive and negative) statistical significance. It is also noticed that when AVAs are dominating by class association with low noise level, there is no significant AVAs in other RSRVs as most of the SR values are below 1.00. However, when class labels are not included, minor disentangled subtle patterns begin to emerge from other RSRVs (FIGS. 19C and 19D) corresponding to PCs with strong/weak variance respectively.

It should be appreciated that the latter problem may be equivalent to an unsupervised method in revealing subgroup AVA patterns without relying on explicit prior knowledge.

Figure 19B:
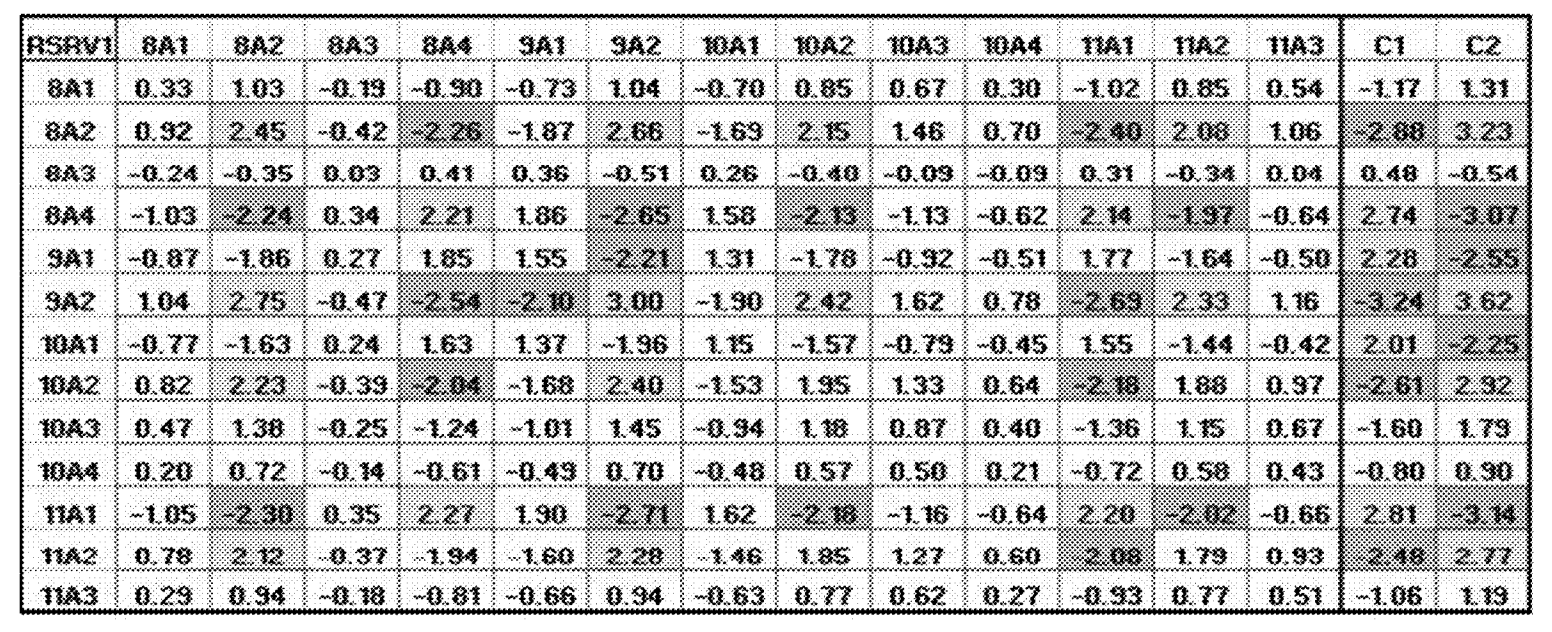

FIGS. 19A to 19D illustrate and example with the UCI dataset of the disentangled SRV Space with strong AVA SR. FIG. 19A illustrates SRV, FIG. 19B illustrates RSRV1 with class labels included. FIG. 19C illustrates RSRV1 when class labels are withdrawn and AVA associating with class still strongly manifested. FIG. 19D illustrates RSRV5 when class labels are not included. Note that the SR are lower but still stand out from the background. Dissimilarity of SR distribution in FIG. 19C and FIG. 19D indicates disentanglements of SR when as shown in SRV in FIG. 19A where they are entangled.

From the corresponding part of SRV (FIG. 19A), RSRV1 (FIG. 19B) with class association, and RSRV1 (FIG. 19C) RSRV5 (FIG. 15D) without class association, it is observed that the first three consist of strong SR (>1.96) associating to $C_1$ and $C_2$, though the SR in FIG. 15C are a little lower. This indicates that without explicit prior knowledge, AVAA may be able to discover the AVAs (FIG. 19C) somewhat equivalent to pattern clustering. Pattern clustering is described in A. K. Wong and G. C. L. Li, "*Simultaneous pattern and data clustering for pattern cluster analysis,*" *IEEE Trans. Knowl. Data Eng.,* vol. 20, no. 7, pp. 911-923, 2008, the contents of which are hereby incorporated by reference.

Results in FIG. 19C show that without relying on class labels, AVAA is still able to come up with almost an equivilant set of AVAs to that in FIG. 19B when class labels are given. One interesting observation was that the disentangled AVAs in some minor PCs only distinctively emerged after strong associating factors like the class labels were removed as observed in RSRV5 (FIG. 19D) and RSRV2 to RSRV4 (not shown). Their SRs are still distinct yet weaker since they reveal the non-dominating yet rarer happenings. When comparing FIGS. 19A and 19B with FIG. 19D, it is observed that the distinct SRs in FIG. 19D are different from those in the others, though the values are a little low (with five over 1.28 and one over 1.03 corresponding to above 80% and 70% confidence level respectively). Nevertheless, they are still distinct from the background. From the C-boxes in FIG. 15D, it is noticed that they are not directly related to classes. This may indicate that they might be governed by some not readily known underlying factors that worth inspecting. It should be appreciated that revealing AVAs and their groupings, as unveiled in different RSRVs corresponding to different orthogonal PCs, the deeper knowledge that have been obscured and deeply buried in the relational data. It could shed light to the understanding of the subtle factors and provide a statistical base to account for new knowledge in factor and predictive analysis.

Figure 20:
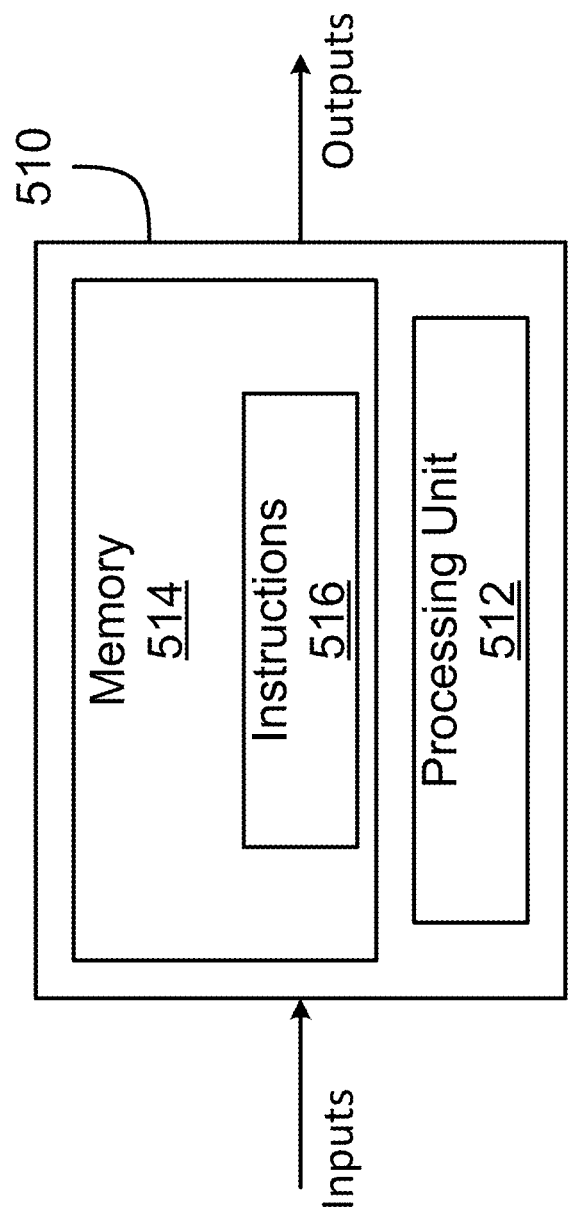
FIG. 20 is a schematic diagram of an example computing system for implementing the method of FIGS. 2 and 10 in accordance with an embodiment.

With reference to FIG. 20, the methods 10 and 20 may be implemented by a computing device 510, comprising a processing unit 512 and a memory 514 which has stored therein computer-executable instructions 516. The processing unit 512 may comprise any suitable devices configured to implement the system such that instructions 516, when executed by the computing device 510 or other programmable apparatus, may cause the functions/acts/steps of the method 10 or 20 as described herein to be executed. The processing unit 512 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 514 may comprise any suitable known or other machine-readable storage medium. The memory 514 may comprise non-transitory computer readable storage medium, for example, but not limited to, an electronic, magnetic, optical, electromagnetic, infrared, or semiconductor system, apparatus, or device, or any suitable combination of the foregoing. The memory 514 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 514 may comprise any storage means (e.g., devices) suitable for retrievably storing machine-readable instructions 516 executable by processing unit 512.

The methods and systems described herein may be implemented in a high level procedural or object oriented programming or scripting language, or a combination thereof, to communicate with or assist in the operation of a computer system, for example the computing device 510. Alternatively, the methods and systems may be implemented in assembly or machine language. The language may be a compiled or interpreted language. Program code for implementing the methods and systems may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems may also be considered to be implemented by way of a non-transitory computer-readable storage medium having a computer program stored thereon. The computer program may comprise computer-readable instructions which cause a computer, or in some embodiments the processing unit 512 of the computing device 510, to operate in a specific and predefined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

The headings used in the detailed description are not intended to be limiting. Various details described under one heading may be applicable under another.

Various aspects of the methods and systems described herein may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be obvious to those skilled in the art that changes and modifications may be made without departing from this invention in its broader aspects. The scope of the following claims should not be limited by the embodiments set forth in the examples, but should be given the broadest reasonable interpretation consistent with the description as a whole.

The invention claimed is:

1. A computer-implemented method for training a machine learning classifier to determine interaction sites between biosequences, comprising:
obtaining, by a processor, a dataset of contact data for a plurality of biomolecule pairs from a database, each one of the biomolecule pairs composed of a biomolecule $r_i$ from a first biosequence and a biomolecule $r_j$ from a second biosequence, the contact data corresponding to a separation distance between $r_i$ and $r_j$;
transforming, by the processor, the contact data to create statistical weights, the transforming including:
accounting, by the processor, a frequency of occurrence of every biomolecule pair ($r_i$, $r_j$) in the contact data to obtain a frequency table;
determining, by the processor, a statistical weight for each frequency of occurrence as a function of a deviation of the frequency of occurrence from an expected frequency to obtain a statistical residual frequency matrix, wherein the statistical residual frequency matrix is considered as a statistical residual vector space such that each row is a vector having coordinates that are statistical residuals of a given biomolecule interaction with other biomolecules corresponding to a column of the statistical residual vector space;
decomposing, by the processor, the statistical residual vector space through principal component decomposition to obtain vector projections on principal components to reveal orthogonal interacting functionality through a strength of corresponding coordinates as reflected by a variance of principal components;
re-projecting, by the processor, the vector projections on the principal components to re-projected statistical residual vector spaces with new vector positions; and
deriving, by the processor, the statistical weights from the re-projected residual vector spaces for each biomolecule pair ($r_i$, $r_j$);
generating, by the processor, a k-dimensional feature vector for each biomolecule pair ($r_i$, $r_j$) and its nearest neighbors, for classifier training, using at least the statistical weights;
creating, by the processor, a training set comprising one or more of the feature vectors for each biomolecule pair ($r_i$, $r_j$);
training, by the processor, a classifier to classify a likelihood of an interaction site, using the training set;
wherein the classifier is operable to classify feature vectors constructed from an input biosequence pair to determine a likelihood that the input biosequence pair is interacting at an interaction site.

2. The method of claim 1, wherein obtaining the dataset comprises obtaining contact data for at least one of protein sequences, DNA sequences, and RNA sequences.

3. The method of claim 1, wherein the biomolecule pairs ($r_i$, $r_j$) are residue pairs for protein sequences.

4. The method of claim 1, wherein decomposing the vector of each row comprises performing Eigen-decomposition and creating a matrix of eigenvectors from eigenvalues as a first set of coordinates, each eigenvector representing underlying orthogonal components of related molecular functions.

5. The method of claim 1, wherein inputting the feature vector to a predictor comprises inputting the feature vector into a predictor trained with a set of training samples maintained at a balanced ratio in each bag.

6. The method of claim 1, wherein generating a k-dimensional feature vector for each biomolecule pair ($r_i$, $r_j$) comprises concatenating the biomolecule pair ($r_i$, $r_j$), at least one neighbor of each biomolecule in the biomolecule pair, coordinates of the projected vectors for each one of the biomolecule pair and the at least one neighbor, and coordinates of the re-projected r-vectors for each one of the biomolecule pair and the at least one neighbor.

7. The method of claim 1, further comprising analyzing the statistical weights in the reprojected statistical residual vector space to reveal specific interacting functions between biomolecules.

8. The method of claim 7, further comprising determining a statistical significance of the specific interaction functions between biomolecules $r_i$ and $r_j$ for a particular interacting function as reflected in the re-projected statistical residual vector space.

9. The method of claim 1, wherein the statistical significance of the frequency of occurrence of each biomolecule pair (ri, rj) comprises determining a statistical weight for each frequency of occurrence as a function of a deviation of the frequency of occurrence from an expected frequency.

10. The method of claim 1, wherein the vector projections on principal components reveals orthogonal interacting functionality through a strength of corresponding coordinates as reflected by a variance of principal components.

11. A system for training a machine learning classifier to determine interaction sites between biosequences, the system comprising:
at least one processor; and
a non-transitory computer-readable memory having stored thereon program instructions executable by the at least one processor for:
obtaining, by the processor, a dataset of contact data for a plurality of biomolecule pairs from a database, each one of the biomolecule pairs composed of a biomolecule $r_i$ from a first biosequence and a biomolecule $r_j$ from a second biosequence, the contact data corresponding to a separation distance between $r_i$ and $r_j$;
transforming, by the processor, the contact data to create statistical weights, the transforming including:
accounting, by the processor, a frequency of occurrence of every biomolecule pair ($r_i$, $r_j$) in the contact data to obtain a frequency table;
determining, by the processor, a statistical weight for each frequency of occurrence as a function of a deviation of the frequency of occurrence from an expected frequency to obtain a statistical residual frequency matrix, wherein the statistical residual frequency matrix is considered as a statistical residual vector space such that each row is a vector having coordinates that are statistical residuals of a given biomolecule interaction with other biomolecules corresponding to a column of the statistical residual vector space;

decomposing, by the processor, the statistical residual vector space through principal component decomposition to obtain vector projections on principal components to reveal orthogonal interacting functionality through a strength of corresponding coordinates as reflected by a variance of principal components;

re-projecting, by the processor, the vector projections on the principal components to re-projected statistical residual vector spaces with new vector positions; and deriving, by the processor, the statistical weights from the re-projected residual vector spaces for each biomolecule pair $(r_i, r_j)$;

generating, by the processor, a k-dimensional feature vector for each biomolecule pair $(r_i, r_j)$ and its nearest neighbors, for classifier training, using at least the statistical weights;

creating, by the processor, a training set comprising one or more of the feature vectors for each biomolecule pair $(r_i, r_j)$;

training, by the processor, a classifier to classify a likelihood of an interaction site, using the training set;

wherein the classifier is operable to classify feature vectors constructed from an input biosequence pair to determine a likelihood that the input biosequence pair is interacting at an interaction site.

12. The system of claim 11, wherein obtaining the dataset comprises obtaining contact data for at least one of protein sequences, DNA sequences, and RNA sequences.

13. The system of claim 11, wherein the biomolecule pairs $(r_i, r_j)$ are residue pairs for protein sequences.

14. The system of claim 11, wherein decomposing the vector of each row comprises performing Eigen-decomposition and creating a matrix of eigenvectors from eigenvalues as a first set of coordinates, each eigenvector representing underlying orthogonal components of related molecular functions.

15. The system of claim 11, wherein inputting the feature vector to a predictor comprises inputting the feature vector into a predictor trained with a set of training samples maintained at a balanced ratio in each bag.

16. The system of claim 11, wherein generating a k-dimensional feature vector for each biomolecule pair $(r_i, r_j)$ comprises concatenating the biomolecule pair $(r_i, r_j)$, at least one neighbor of each biomolecule in the biomolecule pair, coordinates of the projected vectors for each one of the biomolecule pair and the at least one neighbor, and coordinates of the re-projected r-vectors for each one of the biomolecule pair and the at least one neighbor.

17. The system of claim 11, further comprising analyzing the statistical weights in the reprojected statistical residual vector space to reveal specific interacting functions between biomolecules.

18. The system of claim 17, further comprising determining a statistical significance of the specific interaction functions between biomolecules $r_i$ and $r_j$ for a particular interacting function as reflected in the re-projected statistical residual vector space.

19. The system of claim 11, wherein the statistical significance of the frequency of occurrence of each biomolecule pair (ri, rj) comprises determining a statistical weight for each frequency of occurrence as a function of a deviation of the frequency of occurrence from an expected frequency.

20. The system of claim 11, wherein the vector projections on principal components reveals orthogonal interacting functionality through a strength of corresponding coordinates as reflected by a variance of principal components.

* * * * *